US012595449B2

(12) United States Patent
Aschar-Sobbi et al.

(10) Patent No.: US 12,595,449 B2
(45) Date of Patent: *Apr. 7, 2026

(54) INTEGRATED SYSTEM FOR 3D TISSUE CULTURE

(71) Applicant: Valo Health, Inc., Boston, MA (US)

(72) Inventors: Roozbeh Aschar-Sobbi, New York, NY (US); Maw-Lin Kuo, Newark, CA (US); Roger Stenerson, Newark, CA (US); Winston Sun, Newark, CA (US); Dickshitha Thyagharajon, Newark, CA (US); Ya Kevin Thao, Newark, CA (US); Chris Todd, Newark, CA (US); Brian Wilfley, Newark, CA (US)

(73) Assignee: VALO HEALTH, INC., Lexington, MA (US)

( * ) Notice: Subject to any disclaimer, the term of this patent is extended or adjusted under 35 U.S.C. 154(b) by 893 days.

This patent is subject to a terminal disclaimer.

(21) Appl. No.: 17/798,048

(22) PCT Filed: Feb. 3, 2021

(86) PCT No.: PCT/US2021/016317
§ 371 (c)(1),
(2) Date: Aug. 5, 2022

(87) PCT Pub. No.: WO2021/158598
PCT Pub. Date: Aug. 12, 2021

(65) Prior Publication Data
US 2023/0113389 A1     Apr. 13, 2023

Related U.S. Application Data

(60) Provisional application No. 62/971,412, filed on Feb. 7, 2020.

(51) Int. Cl.
*C12M 3/00* (2006.01)
*C12M 1/32* (2006.01)
(Continued)

(52) U.S. Cl.
CPC .......... *C12M 21/08* (2013.01); *C12M 1/3446* (2013.01); *C12M 23/12* (2013.01);
(Continued)

(58) Field of Classification Search
CPC .... C12M 21/08; C12M 1/3446; C12M 23/12; C12M 35/02; C12M 41/48; C12M 41/40; C12N 2513/00; C12N 2533/40
See application file for complete search history.

(56) References Cited

U.S. PATENT DOCUMENTS

2008/0038812 A1     2/2008     Elson et al.
2008/0038813 A1     2/2008     Chen
(Continued)

FOREIGN PATENT DOCUMENTS

AU     2014344726 B2     5/2015
DE     19500498 C2     7/1996
(Continued)

OTHER PUBLICATIONS

Radisic, Mllica, Boyang Zhang, Yimu Zhao, Keith Yeager U.S. Appl. No. 17/798,047. "A Microphysiological Platform with Embedded Electrodes for 3D Tissue Culture". Earliest Effective filed Feb. 7, 2020. (Year: 2020).*
(Continued)

*Primary Examiner* — Michael L Hobbs
(74) *Attorney, Agent, or Firm* — MARSHALL, GERSTEIN & BORUN LLP

(57) ABSTRACT

Embodiments described herein relate generally to devices, apparatuses, and systems with embedded electrodes for growing, maintaining, and/or using 3D tissues in vitro. The
(Continued)

100 devices, apparatuses, and systems described herein can provide scalable, automated tissue stimulation.

13 Claims, 24 Drawing Sheets

(51) Int. Cl.

| | | |
|---|---|---|
| *C12M 1/34* | (2006.01) | |
| *C12M 1/36* | (2006.01) | |
| *C12M 1/42* | (2006.01) | |

(52) U.S. Cl.
CPC ............ *C12M 35/02* (2013.01); *C12M 41/48* (2013.01); *C12N 2513/00* (2013.01); *C12N 2533/40* (2013.01)

(56) References Cited

U.S. PATENT DOCUMENTS

| | | | | |
|---|---|---|---|---|
| 2011/0118143 A1* | 5/2011 | Wakatsuki | .............. | C40B 30/06 |
| | | | | 506/10 |
| 2015/0313704 A1* | 11/2015 | Thavandiran | ........ | C12N 5/0657 |
| | | | | 623/23.72 |
| 2016/0282338 A1 | 9/2016 | Miklas et al. | | |
| 2017/0016875 A1 | 1/2017 | Parker et al. | | |

FOREIGN PATENT DOCUMENTS

| | | |
|---|---|---|
| JP | 2005-334456 A | 12/2005 |
| JP | 2006-311887 A | 11/2006 |
| JP | 2013-074863 A | 4/2013 |
| KR | 10-2008-0030297 A | 4/2008 |
| KR | 1020100122874 A | 11/2010 |
| KR | 1020110014362 A | 2/2011 |
| KR | 10-1217686 B1 | 1/2013 |
| KR | 1020160145535 A | 12/2016 |
| KR | 1020180095649 A | 8/2018 |
| WO | WO-2012/170490 A2 | 12/2012 |
| WO | WO-2013/056019 A1 | 4/2013 |
| WO | WO-2015/061907 A1 | 5/2015 |
| WO | WO-2019/056019 A1 | 3/2019 |

OTHER PUBLICATIONS

Zhao, Yimu, "Biowire II Platform: High Fidelity Heart-on-a-chip for Drug Screening and Disease Modeling," PhD thesis, Department of Chemical Engineering and Applied Chemistry University of Toronto, Nov. 2019, pp. 1-172.
Wang et al., "Biowire Model of Interstitial and Focal Cardiac Fibrosis," ACS Central Science, 2019, vol. 5, pp. 1146-1158.
Zhao et al., "A Platform for Generation of Chamber-Specific Cardiac Tissues and Disease Modeling," Cell, Feb. 7, 2019, vol. 175, pp. 913-927.
International Search Report and Written Opinion dated Jul. 28, 2021, from application No. PCT/US2021/016317, 16 pages.
International Search Report and Written Opinion dated Oct. 30, 2020, from application No. PCT/US2020/017195, 9 pages.
Nunes, et al., "Biowire: a platform for maturation of human pluripotent stem cell-derived cardiomyocytes: Supplementary Figures", Nature Methods, Jun. 23, 2013, vol. 10, No. 8, pp. 781-787.
Sidorov, et al., "I-Wire Heart-on-a-Chip I: Three-dimensional cardiac tissue constructs for physiology and pharmacology", Acta Biomater, Jan. 15, 2017, vol. 48, pp. 68-78.
Lai et al., "InVADE: Integrated Vasculature for Assessing Dynamic Events," Advanced Functional Materials, 2017, 27, 1703524, 11 pages.
Zhao et al., "A Multimaterial Microphysiological Platform Enabled by Rapid Casting of Elastic Microwires," Advanced Healthcare Materials, Aug. 2019, 1801187, 10 pages.
Korean Patent Application No. 10-2022-7030585, Office Action, dated May 21, 2025.
KR10-2022-7030585 Notice of Allowance issued Jan. 26, 2026.

* cited by examiner

Suspended polymer wire

In distilled water    Soaked overnight    Air dried

Force probe

Wire

Post-processing at 70 °C for 2 days $$y = 1.57 \times 10^{-5} x^3 + 3.42 \times 10^{-3} x^2 + 4.76 \times 10^{-2} x$$

Post-processing at 70 °C for 4 days $$y = 2.56 \times 10^{-5} x^3 + 1.12 \times 10^{-3} x^2 + 3.91 \times 10^{-1} x$$

Post-processing at 70 °C for 6 days $$y = 7.68 \times 10^{-6} x^3 + 7.30 \times 10^{-3} x^2 + 3.71 \times 10^{-1} x$$

High-throughput imaging cytometer

Sputtered gold electrodes          Sputtered gold electrodes

Scratch $$\text{Voltage Drop} = \frac{(\text{Voltage Source} - \text{Voltage}_{well})}{\text{Voltage Source}} \times 100\%$$

300

330

332

Memory

336

334

Processor

320

User Interface

340

316

312

310

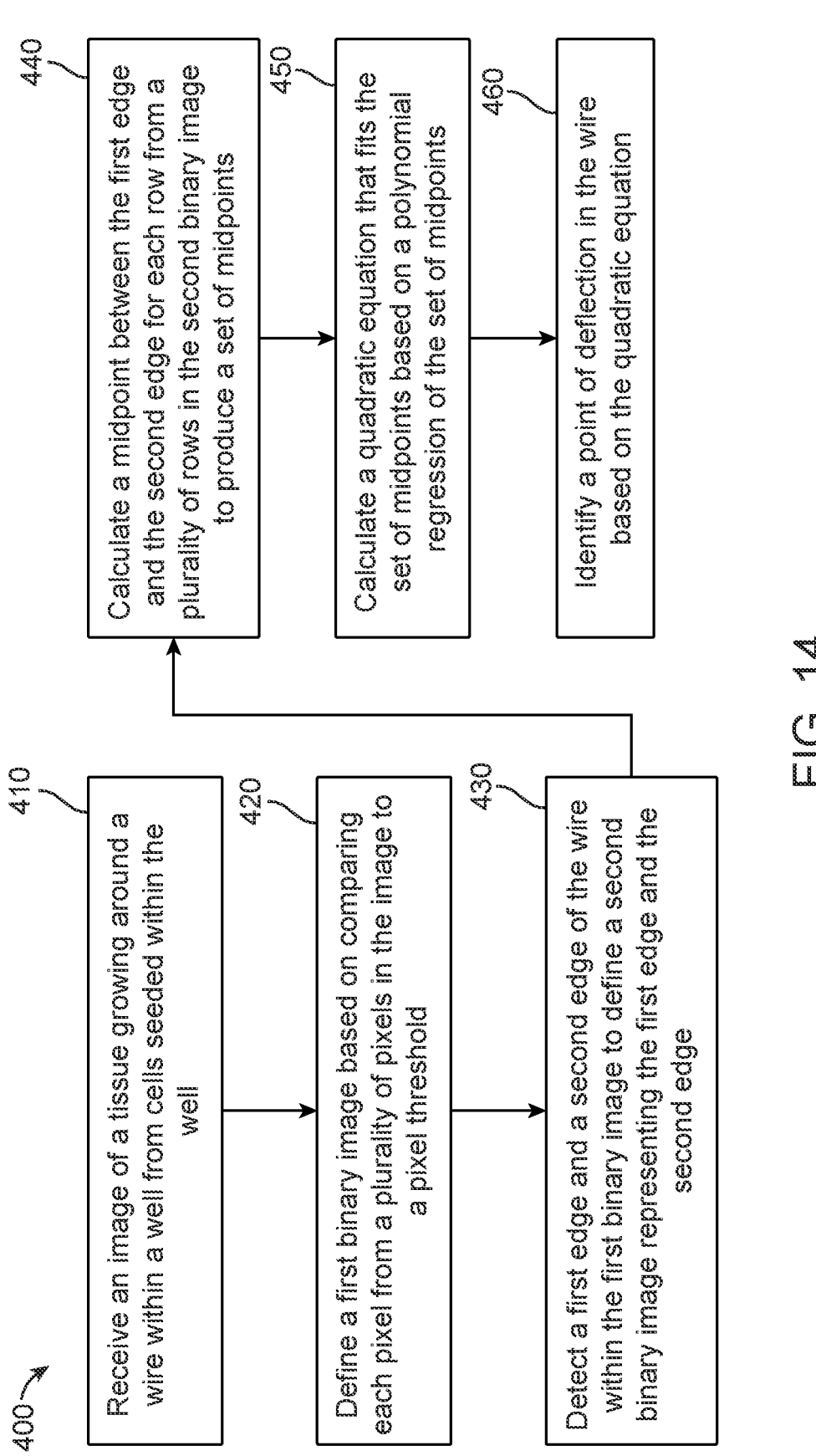

400

410 Receive an image of a tissue growing around a wire within a well from cells seeded within the well 420 Define a first binary image based on comparing each pixel from a plurality of pixels in the image to a pixel threshold 430 Detect a first edge and a second edge of the wire within the first binary image to define a second binary image representing the first edge and the second edge 440 Calculate a midpoint between the first edge and the second edge for each row from a plurality of rows in the second binary image to produce a set of midpoints 450 Calculate a quadratic equation that fits the set of midpoints based on a polynomial regression of the set of midpoints 460 Identify a point of deflection in the wire based on the quadratic equation

FIG. 14

Mid-points

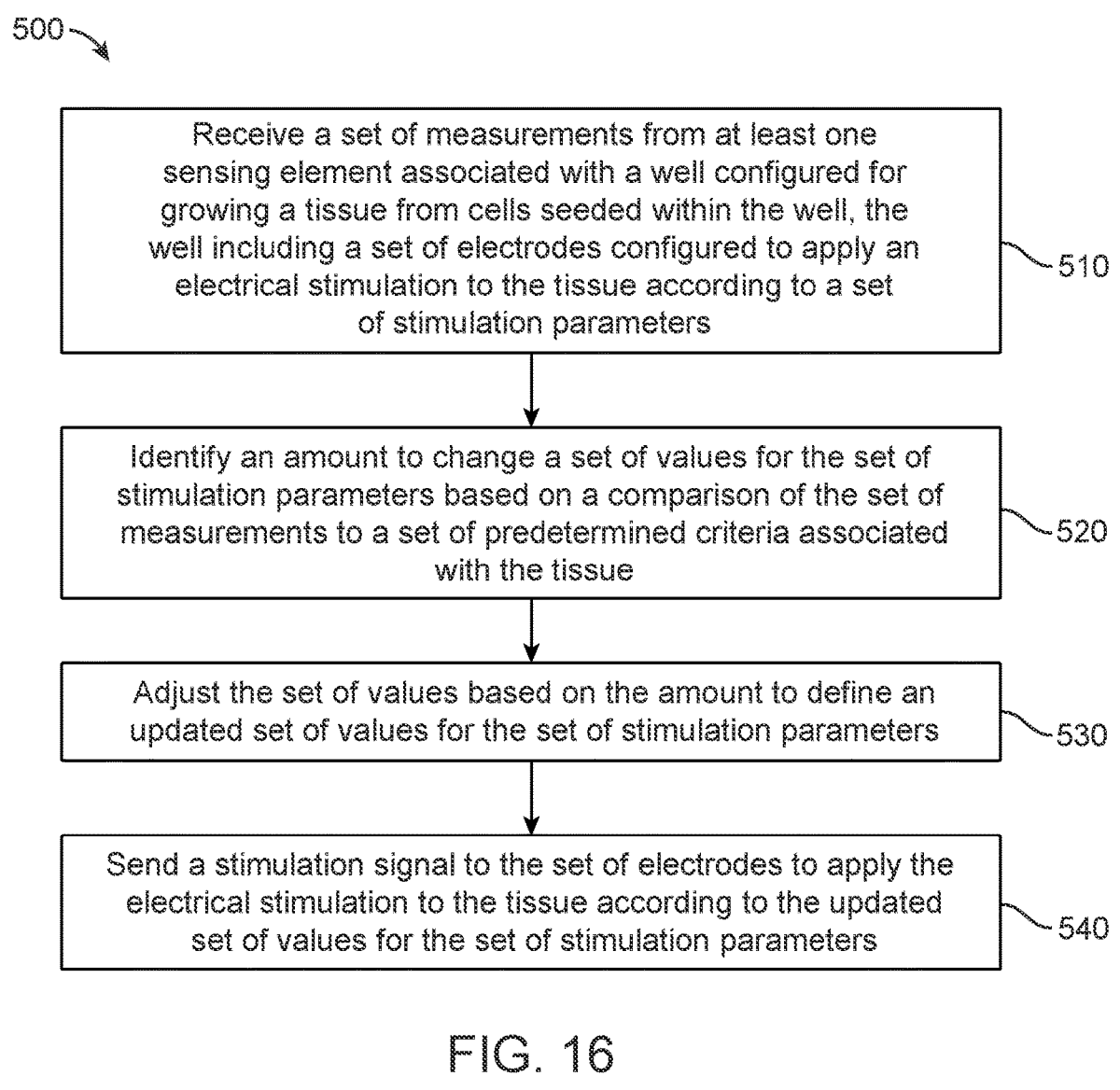

500

Receive a set of measurements from at least one
sensing element associated with a well configured for
growing a tissue from cells seeded within the well, the
well including a set of electrodes configured to apply an
electrical stimulation to the tissue according to a set
of stimulation parameters                                        510

Identify an amount to change a set of values for the set of
stimulation parameters based on a comparison of the set of
measurements to a set of predetermined criteria associated
with the tissue                                                  520

Adjust the set of values based on the amount to define an
updated set of values for the set of stimulation parameters      530

Send a stimulation signal to the set of electrodes to apply the
electrical stimulation to the tissue according to the updated
set of values for the set of stimulation parameters              540

FIG. 16

INTEGRATED SYSTEM FOR 3D TISSUE CULTURE

RELATED APPLICATIONS

This application is a 371 U.S. national phase application of PCT/US2021/016317, filed on Feb. 3, 2021, which claims priority to and the benefit of U.S. Provisional Patent Application No. 62/971,412, filed on Feb. 7, 2020, the disclosures of each of which are hereby incorporated by reference in their entireties.

TECHNICAL FIELD

The present disclosure relates generally to platforms with embedded electrodes for growing three-dimensional (3D) tissues in vitro.

BACKGROUND

Due to escalating drug developmental costs and limitations of cardiotoxicity screening, there is an urgent need to develop robust in vitro 3D tissue culture platforms that can both facilitate the culture of human cardiac tissues and provide noninvasive functional readouts predictive of cardiotoxicity in clinical settings. However, such platforms commonly require complex fabrication procedures that are difficult to scale up to high-throughput testing platforms.

Cardiotoxicity is a major cause of drug failure at the later stages of clinical trials and it is linked to a number of postmarket withdrawals. Validating the safety of candidate drugs and eliminating unqualified candidates as early as possible is key for reducing the costs of drug discovery and preventing patient fatality. Although conventional monolayer cultures with immortalized cell lines enable high-throughput screening, they have limited relevance to native myocardium due to the lack of tissue level function and morphological organization. Engineered cardiac tissues from human stem cell derived cardiomyocytes have been shown to more closely mimic the myofiber bundles of the native cardiac muscle, exhibiting an aligned sarcomere structure and remarkable levels of contractile forces. However, manufacturing reproducible 3D tissues in large quantities requires complicated fabrication processes, which involve building hollow or suspended microstructures that are important to promote functional tissue formation. Furthermore, detecting cardiotoxicity also requires functional readouts from engineered cardiac tissues.

Built-in sensors have been incorporated in many microphysiological platforms. For example, thin muscle films were created on top of a thin layer of polydimethylsiloxane (PDMS) or a polyurethane film. Deformation of the films could be easily modeled and correlated to force of contraction generated by overlaid cardiomyocytes. More recently, an electrical circuit was embedded in the thin polymer film using 3D printing. This technology can translate electrical signal of an embedded resistor into contractile dynamics using modeling techniques. However, these systems only allow culture of cell monolayers of structures that are several cell layers thick. Widely used two-post platforms adopted PDMS posts as force sensors to noninvasively report force of contraction from a 3D tissue. However, cultivated tissues are prone to slipping off from the posts resulting in device failure. In addition, these devices rely on the use of PDMS, which is prone to drug absorption due to its hydrophobic nature.

SUMMARY

One aspect of the present disclosure relates to a device comprising: a substrate; at least one pair of electrodes embedded at least partially in the substrate, the pair of electrodes having a first electrode and a second electrode separated by a gap; at least one well having a bottom on the substrate, a first end in contact with the first electrode, and a second end in contact with the second electrode, the well configured for growing a tissue from cells seeded therein, wherein the pair of electrodes is configured to apply an electrical stimulation to the tissue; and at least two elastic sensing elements disposed across the well such that there is a gap between the sensing elements and the bottom of the well, wherein the sensing elements are configured to: (a) permit attachment of the tissue formed therebetween, thereby suspending the tissue above the bottom of the well, and (b) deform in response to the contractile force exerted on the sensing elements by the tissue, thereby simulating a physiological environment that is native to the tissue and/or permitting measurement of the contractile force.

In some embodiments, the device comprises two or more wells, such as 6 wells, 12 wells, 24 wells, 48 wells, or 96 wells.

In some embodiments, the pair of electrodes is fully embedded in the substrate.

In some embodiments, the electrodes comprise conductive carbon, gold, platinum, palladium, stainless steel, tin, tungsten, titanium, or a combination thereof.

In some embodiments, the conductive carbon is non-porous.

In some embodiments, the first electrode and the second electrode are separated by a gap in the range of 1 mm to 5 cm.

In some embodiments, the first electrode is parallel or substantially parallel to the second electrode.

In some embodiments, the device comprises two or more pairs of electrodes, wherein at least one well is positioned in between each pair of electrodes.

In some embodiments, each of the electrodes is parallel or substantially parallel to each other.

In some embodiments, the pair of electrodes is coupled to a stimulator, the stimulator configured to apply an electrical stimulation between the pair of electrodes.

In some embodiments, the device comprises two or more pairs of electrodes, wherein two or more wells are positioned between each pair of electrodes, and wherein the stimulator is configured to control the electrical stimulation between each pair of electrodes independently.

In some embodiments, the device comprises 2 to 25 sensing elements per well.

In some embodiments, the sensing elements comprise a polymer. In some embodiments, the polymer is at least one of polylactic acid, poly(lactic-co-glycolic) acid, poly(caprolactone), polyglycolide, polylactide, polyhydroxybutyrate, polyhydroxyalcanoic acid, chitosan, hyaluronic acid, a hydrogel, poly(2-hydroxyethyl-methacrylate), poly(ethylene glycol), poly(L-lactide) (PLA), poly(dimethysiloxane) (PDMS), poly(methylmethacrylate) (PMMA), poly(glycerol sebacate), poly(octamethylene maleate (anhydride) citrate) (POMaC), POMaC without citric acid, poly(ε-caprolactone), polyurethane, silk, a nanofabricated material, a co-polymer, a blended polymer, or a combination thereof. In some embodiments, the polymer is POMaC.

In some embodiments, the polymer has mechanical properties tunable during a polymerization reaction.

In some embodiments, the sensing elements are porous, thereby permitting delivery of nutrients and growth factors to the cardiac tissue.

In some embodiments, the sensing elements have an elasticity from about 20 kPa to 0.5 MPa.

In some embodiments, the sensing elements has a wire shape.

In some embodiments, the well is configured to have a longitudinal axis.

In some embodiments, the sensing elements have an orientation that is perpendicular, parallel, or diagonal relative to the longitudinal axis of the well.

In some embodiments, the substrate comprises a polymer. In some embodiments, the polymer is rigid. In some embodiments, the polymer is polystyrene or polycarbonate.

In some embodiments, the cells are seeded in a hydrogel.

In some embodiments, the cells are selected from cardiomyocytes, fibroblasts, skeletal muscle cells, hepatocytes, renal cells, chondrocytes, skin cells, contractile cells, blood cells, immune system cells, germ cells, neural cells, epithelial cells, hormone secreting cells, bone marrow cells, stem cells, tumor cells, smooth muscle cells, endothelial cells, fibroblasts, adipose derived stem cells, mesenchymal stem cells, progenitor cells, or a combination thereof.

One aspect of the present disclosure relates to a non-transitory processor-readable medium storing code representing instructions to be executed by a processor, the instructions comprising code to cause the processor to: receive a set of measurements from at least one sensing element associated with a well configured for growing a tissue from cells seeded within the well, the well including a set of electrodes configured to apply an electrical stimulation to the tissue according to a set of stimulation parameters; identify an amount to change a set of values for the set of stimulation parameters based on a comparison of the set of measurements to a set of predetermined criteria associated with the tissue; adjust the set of values based on the amount to define an updated set of values for the set of stimulation parameters; and send a stimulation signal to the set of electrodes to apply the electrical stimulation to the tissue according to the updated set of values for the set of stimulation parameters.

In some embodiments, the set of stimulation parameters includes at least one of stimulation voltage, stimulation frequency, or stimulation time.

In some embodiments, the at least one sensing element includes at least two elastic sensing elements disposed across the well such that there is a gap between the sensing elements and a bottom of the well.

In some embodiments, an initial set of values for the set of stimulation parameters is selected based on a predetermined stimulation protocol.

In some embodiments, the code to cause the processor to identify includes code to cause the processor to identify an amount to reduce a stimulation voltage based on the set of measurements meeting a maturity criterion for the tissue.

In some embodiments, the code to cause the processor to identify includes code to cause the processor to identify an amount to increase a stimulation voltage based on the set of measurements not meeting an excitation criterion for the tissue.

In some embodiments, the code to cause the processor to receive the set of measurements includes code to cause the processor to periodically receive an instance of the set of measurements and store the instance of the set of measurements in a memory.

One aspect of the present disclosure relates to an apparatus, comprising: a memory; and a processor operatively coupled to the memory, the processor configured to: receive an image of a tissue growing around a wire within a well from cells seeded within the well, define a first binary image based on comparing each pixel from a plurality of pixels in the image to a pixel threshold, detect a first edge and a second edge of the wire within the first binary image to define a second binary image representing the first edge and the second edge, calculate a midpoint between the first edge and the second edge for each row from a plurality of rows in the second binary image to produce a set of midpoints, calculate a quadratic equation that fits the set of midpoints based on a polynomial regression of the set of midpoints, and identify a point of deflection in the wire based on the quadratic equation.

In some embodiments, the well includes a set of electrodes configured to apply an electrical stimulation to the tissue according to a set of stimulation parameters, the processor further configured to: adjust a set of values for the set of stimulation parameters based on the point of deflection in the wire meeting a predetermined criterion to define an updated set of values for the set of stimulation parameters; and send a stimulation signal to the set of electrodes to apply the electrical stimulation to the tissue according to the updated set of values for the set of stimulation parameters.

In some embodiments, the processor is configured to detect the first edge and the second edge using a Sobel operator.

In some embodiments, the processor is configured to define the first binary image using Otsu's method.

In some embodiments, the processor is configured to remove artifact pixels from the first binary image using an opening operator prior to detecting the first edge and the second edge of the wire within the first binary image.

In some embodiments, the processor is configured to smooth the first binary image using a closing operator prior to detecting the first edge and the second edge of the wire within the first binary image.

In some embodiments, the processor is configured to complete, prior to calculating the midpoint, a portion of the first edge or a portion of the second edge not included within the second binary image such that each row from the plurality of rows in the second binary image includes a portion of the first edge and a portion of the second edge.

In some embodiments, the processor is configured to calculate the amount of contractile force exerted on the wire by the tissue based on the point of deflection.

In some embodiments, the processor is configured to calculate the amount of passive tension exerted on the wire by the tissue based on the point of deflection.

One aspect of the present disclosure relates to a system comprising: two or more devices described herein; and a stimulator having two or more driver boards, wherein each driver board is configured to apply an electrical stimulation between each pair of electrodes of each device, thereby permitting the stimulator to independently control the application of the electrical stimulation between each pair of electrodes.

In some embodiments, the system further comprises an interface tray having a hinged lid and configured to couple the devices electrically to the stimulator.

In some embodiments, the system further comprises an optical microscope configured to produce an image of the sensing elements and/or tissue in each device.

In some embodiments, the system further comprises a computing device coupled to the microscope and configured to analyze the image and/or control the stimulator.

In some embodiments, the computing device comprises a non-transitory processor-readable medium described herein.

In some embodiments, the computing device comprises an apparatus described herein.

BRIEF DESCRIPTION OF THE DRAWINGS

FIG. 2A shows the incorporation of carbon electrodes to Biowire plate base.

FIG. 2B shows casting of polymer microwires to Biowire plate base.

FIG. 2C shows the assembled Biowire plate and representative image of a cardiac tissue cultured in the Biowire chamber and suspended across two polymer wires in parallel. Scale bar, 1 mm.

FIG. 3A is an illustration of hot-embossed polystyrene plate base embedded with carbon electrodes.

FIG. 3B is an image of a polystyrene plate base embedded with carbon electrodes. The top surface of the carbon electrode is exposed.

FIG. 3C shows a Biowire plate completely assembled with both polymer wires and carbon electrodes viewed from the back side. Arrows indicate the location of carbon electrodes and tissue chambers.

FIG. 4A is an illustration of polymer injection molding, UV crosslinking, wire casting, and mold release.

FIG. 4B shows images of polymer injection with capillary forces showing the polymer solution was able to perfuse across the suspended microchannel above the tissue chamber.

FIG. 4C is an image of polymer wires successfully suspended across tissue chambers after mold removal.

FIG. 4D shows images of the assembled Biowire plate soaked in distilled water (1) after 1 min, (2) after 24 h, and (3) after air-drying. Scale bar, 1 mm.

FIG. 5A shows images of a force probe used to deflect the polymer wire to correlate force and displacement.

FIGS. 5B-5D show force-displacement curves for the POMaC wires obtained after (FIG. 5B) two days (n=8), (FIG. 5C) four days (n=3), and (FIG. 5D) six days (n=7) of postprocessing baking at 70° C. The graphs show the raw data traces for individual force-displacement curves with 95% confidence intervals around the mean value, the polynomial equations and $R^2$ values of the fitted curves.

FIG. 6A is a bright-field image of cardiac tissues cultured in Biowire II 96-well plates. The final image was stitched from multiple images.

FIG. 6B is a fluorescent image of a cardiac tissue cultured in a 96-well plate device stained for sarcomeric-α-actinin (green) and F-actin (red). Scale bar, 30 μm. (n=3).

FIG. 6C is a fluorescent image of cardiac tissues imaged automatically in a SpectraMax image cytometer. The images clearly show the autofluorescent polymer wires in green, potentially enabling the tracking of wire displacement over time in high-throughput. Final image stitched from multiple images. (n=4) Scale bar, 1 mm.

FIG. 7A shows tissue dimensions stabilized after seven days of self-organization observed through (FIG. 7B) daily representative images (n=3). Enhanced electrical properties were indicated by a (FIG. 7C) decreasing trend of excitation threshold and (FIG. 7D) significantly increased maximum capture rate (Student's t-test, n=6) comparing day 7 (before electrical conditioning) and day 19 (end point). The 96-well plate device enables nondestructive force readouts and beating characterization of cultured tissues. Quantification of (FIG. 7E) passive tension, active force, (FIG. 7F) time of contraction, relaxation, and the total duration, (FIG. 7G) contraction and relaxation slopes were compared at days 7 and 19 (n=3). FIG. 7H shows representative traces showing the responses of cultured tissues to thapsigargin at the end point of electrical stimulation (day 19) (n=2). Data are presented as mean±standard deviation and differences between experimental groups were analyzed by Student's t-test. *p<0.05 was considered significant for all the tests.

FIG. 8A is a schematic of the Biowire 96-well plate fabrication protocol.

FIG. 8B shows the dimensions of the PDMS mold for the polymer wire perfusion (unit is in millimeter). Feature height is 200 μm.

FIG. 8C shows the dimensions of the polystyrene plate base (unit is in millimeter). Feature height is 200 μm.

FIG. 9A shows images of the back side of a Biowire 96-well plate with sputtered gold electrodes. Insets show variation in coating thickness for electrodes at a different location across the entire plate which has a width of 120 mm.

FIG. 9B is an image of a scratch created by attempting to connect to the electrode with alligator clamps. Surface scratch like this could easily break the connection of the entire electrode circuit.

FIG. 10A shows the percentage of the voltage drop across the embedded carbon electrodes between wells in different rows of the plate (n=3). Three wells from each row are used in the measurement.

FIG. 10B shows the equation used to calculate voltage drop. Data are presented as mean±standard deviation and differences between experimental groups were analyzed by one way ANOVA. P<0.05 was considered significant for all the tests.

FIG. 11A shows the forces at 100 μm displacement of POMaC wires from each well; displayed both figure and heat map (n≥4). The displacement forces from wires in each well are shown as a heat map. White boxes indicate wells with missing or defected wires that are visually detectable. The two outermost columns were omitted from the measurements on purpose, as non-uniformities were found due to uneven pressure at the edges.

FIG. 11B shows the consistency of POMaC wires from all wells at displacements of 50 μm, 100 μm and 150 μm (n=70).

FIG. 11C shows representative tensile and relaxation curve of a POMaC wire. Data are presented as a mean±standard deviation and differences between experimental groups were analyzed by one way ANOVA. P<0.05 was considered significant for all the tests.

FIG. 14 is a flowchart illustrating a method of image processing for a 3D tissue culture, according to some embodiments of the present disclosure.

FIG. 16 is a flowchart illustrating a method of operating a tissue culture, according to some embodiments of the present disclosure.

DETAILED DESCRIPTION

The present disclosure provides devices, apparatuses, and systems with embedded electrodes for growing, maintaining, and/or using 3D tissues in vitro. As the electrodes are physically embedded in the substrates of the devices, the electrodes can provide electrical leads for a stimulator to apply current directly to the embedded electrodes, such that the tissues in the devices are already in a position to receive electrical stimulation as well as media and nutrients without being moved to another dish or device. The devices, apparatuses, and systems described herein can be used in a variety of applications including drug testing. By exposing the tissue to a test agent, changes in the contractility and/or passive tension of the tissue can be used to evaluate the efficacy, safety, and/or toxicity of the test agent.

Figure 1:
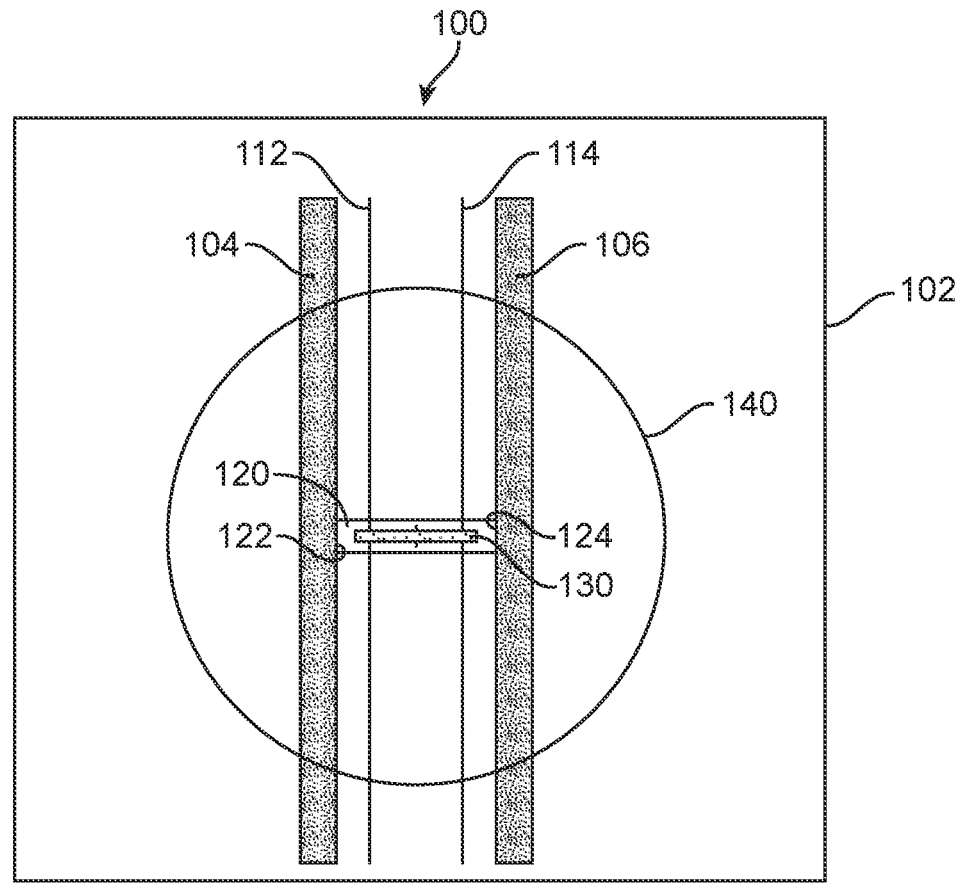
FIG. 1 is a device 100 having embedded electrodes in accordance with some embodiments of the present disclosure.

One aspect of the present disclosure relates to a device 100 of FIG. 1. The device 100 can include a substrate 102, a pair of electrodes including a first electrode 104 and a second electrode 106, a first sensing element 112, a second sensing element 114, and a well 120.

The substrate 102 can include a polymer. In some embodiments, the polymer can be rigid, has high optical clarity, and/or is medically compatible. In some embodiments, the polymer can include polystyrene or polycarbonate.

The pair of electrodes is at least partially embedded in the substrate 102. In some embodiments, the pair of electrodes is fully embedded in the substrate 102. In some embodiments, the first electrode 104 is parallel or substantially parallel to the second electrode 106.

The first electrode 104 and the second electrode 106 can be separated by a gap. The gap can have a width of at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, or at least about 7 mm. The gap can have a width of no more than about 10 cm, no more than about 9.5 cm, no more than about 9 cm, no more than about 8.5 cm, no more than about 8 cm, no more than about 7.5 cm, no more than about 7 cm, no more than about 6.5 cm, no more than about 6 cm, no more than about 5.5 cm, no more than about 5 cm, no more than about 4.5 cm, no more than about 4 cm, no more than about 3.5 cm, no more than about 3 cm, no more than about 2.5 cm, no more than about 2 cm, no more than about 1.5 cm, or no more than about 1 cm.

Combinations of the above-referenced ranges for the width of the gap are also possible (e.g., at least about 1 mm to no more than about 10 cm, at least about 1 mm to no more than about 5 cm, or at least about 5 mm to no more than about 1.5 cm).

Each electrode can include conductive carbon, gold, platinum, palladium, stainless steel, tin, tungsten, titanium, or a combination thereof. Further examples of conductive materials for tissue stimulation can be found at Merrill et al., "Electrical Stimulation of Excitable Tissue: Design of Efficacious and Safe Protocols," J. of Neuroscience Methods 2005, 141, 171-198; Tandon et al., "Characterization of Electrical Stimulation Electrodes for Cardiac Tissue Engineering," Proceedings of the 28th IEEE, pages 845-848, the contents of each of which are incorporated herein by reference.

In some embodiments, the conductive carbon is non-porous, e.g., glassy carbon. Non-porous carbon can prevent test compounds from being absorbed by the carbon. In some embodiments, the carbon electrodes are not epoxy-enforced carbon electrodes.

The well 120 has a bottom on the substrate 102, a first end 122 in contact with the first electrode 104, and a second end 124 in contact with the second electrode 106. The well can be configured for growing a tissue 130 from cells seeded therein. The pair of electrodes can be configured to apply an electrical stimulation to the tissue 130.

The shape of the well 120 is not limited in any particular manner and can be square, rectangular, circular, oval, oblong, triangular, or any combination of shapes. The other dimensions of the well 120 also may vary in any suitable manner. For example, the depth of the well 120, height of the well 120, and length of the well 120, and the overall volume of the well 120 may be varied in any suitable way.

For example, the length, height, or width of the well 120 can be between about 0.1-1 mm, between about 0.2-2 mm, between about 0.3-3 mm, between about 0.4-4 mm, between about 0.5-5 mm, between about 0.6-6 mm, between about 0.7-7 mm, between about 0.8-8 mm, between about 0.9-9 mm, between about 1-10 mm, between about 1-100 mm, or between about 10-100 mm.

The well 120 can be characterized by a longitudinal axis. The longitudinal axis can be along the length of the well 120.

The surface of the well 120 may also be modified with any suitable surface treatments, including chemical modifications (such as, for example, ligands, charged substances, bind agents, growth factors, antibiotics, antifungal agents), or physical modifications (such as, for example, spikes, curved portions, folds, pores, uneven portions, or various shapes and topographies) which may facilitate the tissue culture process.

In some embodiments, the well 120 can be positioned inside a cell culture well 140. Culture medium can be added to the cell culture well 140 for growing and/or sustaining the tissue 130.

The first sensing element 112 and the second sensing element 114 are disposed across the well 120 such that there is a gap between the bottom of the well 120 and the sensing elements 112 and 114. The sensing elements 112 and 114 can be configured to: (a) permit attachment of the tissue 130 formed therebetween, thereby suspending the tissue 130 above the bottom of the well 120, and (b) deform in response to the contractile force exerted on the sensing elements 112 and 114 by the tissue 130, thereby simulating a physiological environment that is native to the tissue 130 and/or permitting measurement of the contractile force.

The sensing elements 112 and 114 can have an orientation that is perpendicular or substantially perpendicular to the longitudinal axis of the well 120. The tissue 130 can be aligned in the same or substantially the same direction as the longitudinal axis of the well 120.

The device 100 can include at least 2 sensing elements per well, at least 3 sensing elements per well, at least 4 sensing elements per well, or at least 5 sensing elements per well. The device 100 can include no more than 25 sensing elements per well, no more than 20 sensing elements per well, no more than 18 sensing elements per well, no more than 15 sensing elements per well, or no more than 10 sensing elements per well.

Combinations of the above-referenced ranges for the number of sensing elements per well are also possible (e.g., at least 2 to no more than 25 per well, at least 2 to no more than 20 per well, or at least 2 to no more than about 10 per well). Any number of sensing elements per well may be provided so long as there is the ability for a tissue to form around each of the sensing elements and become joined therebetween such that the tissue is suspended above the bottom of the well.

The sensing elements can include a polymer. The polymer can be synthetic or biologic. The polymer can also be biodegradable or non-biodegradable.

The sensing elements can comprise a polymer having a Young's modulus similar to that of the tissue supported thereon. For example, the Young's modulus of the polymer can be within ±2000% of the Young's modulus of the tissue; the Young's modulus of the polymer can be within ±1000% of the Young's modulus of the tissue; the Young's modulus of the polymer can be within ±500% of the Young's modulus of the tissue; the Young's modulus of the polymer can be within ±250% of the Young's modulus of the tissue; the Young's modulus of the polymer can be within ±100% of the Young's modulus of the tissue; the Young's modulus of the polymer can be within ±50% of the Young's modulus of the tissue; the Young's modulus of the polymer can be within ±30% of the Young's modulus of the tissue; the Young's modulus of the polymer can be within ±25% of the Young's modulus of the tissue; the Young's modulus of the polymer can be within ±20% of the Young's modulus of the tissue; the Young's modulus of the polymer can be within ±15% of the Young's modulus of the tissue; or the Young's modulus of the polymer can be within ±10% of the Young's modulus of the tissue.

In some embodiments, the sensing elements can comprise a polymer having a Young's modulus in the range of 10 kPa to 800 kPa. For example, the polymer can have a Young's modulus in the range of 20 kPa to 700 kPa, 20 kPa to 600 kPa, 20 kPa to 500 kPa, 50 kPa to 500 kPa, or 100 kPa to 500 kPa. In some embodiments, the polymer can have a Young's modulus of about 150 kPa, about 200 kPa, about 250 kPa, about 300 kPa, about 350 kPa, about 400 kPa, about 450 kPa, about 500 kPa, or about 550 kPa.

In some embodiments, the sensing elements can comprise a polymer whose mechanical properties are tunable by controlling the polymerization using different crosslinking energy. Tunability can also be controlled by the ratio of the mixtures of polymer units during the polymerization reaction.

In some embodiments, the polymer can be at least one of polylactic acid, poly(lactic-co-glycolic) acid, poly(caprolactone), polyglycolide, polylactide, polyhydroxobutyrate, polyhydroxyalcanoic acid, chitosan, hyaluronic acid, a hydrogel, poly(2-hydroxyethyl-methacrylate), poly(ethylene glycol), poly(L-lactide) (PLA), poly(dimethysiloxane) (PDMS), poly(methylmethacrylate) (PMMA), poly(glycerol sebacate), poly(octamethylene maleate (anhydride) citrate) (POMaC), POMaC without citric acid, poly(ε-caprolactone), polyurethane, silk, a nanofabricated material, a copolymer, a blended polymer, or a combination thereof.

The shape, thickness, length, orientation, and surface topographical properties of the sensing elements can vary any number of suitable ways so long as the sensing elements are capable of deforming, bending, or otherwise changing shape in response to the contractile action or activity of the tissue connected therebetween, and that such deforming, bending, or otherwise shape changing can be reliably measured. In some embodiments, the sensing elements are in the form of wires, e.g., polymer wires.

In some embodiments, the sensing elements are porous, thereby permitting delivery of nutrients and growth factors to the tissue 130.

To produce the tissue 130, the cells can be seeded in a hydrogel. The cells can be selected from cardiomyocytes, fibroblasts, skeletal muscle cells, hepatocytes, renal cells, chondrocytes, skin cells, contractile cells, blood cells, immune system cells, germ cells, neural cells, epithelial cells, hormone secreting cells, bone marrow cells, stem cells, tumor cells, smooth muscle cells, endothelial cells, fibroblasts, adipose derived stem cells, mesenchymal stem cells, progenitor cells, or a combination thereof.

In some embodiments, the hydrogel comprises collagen or a collagen derivative, intestinal submucosa or a derivative thereof, cellulose or a cellulose derivative, a proteoglycan, heparin sulfate, chondroitin sulfate, keratin sulfate, hyaluronic acid, elastin, fibronectin, thrombin, laminin, fibrin, chitosan, alginate, Matrigel®, Geltrex®, agarose, decellularized extracellular matrix, polyethylene glycol or a derivative thereof, silicone or a derivative thereof, or a combination thereof. In some embodiments, the hydrogel comprises Matrigel®.

The present disclosure also provides a multi-well device having a plurality of device 100 on a single substrate (e.g., a single plate). In some embodiments, the multi-well device can include a plurality of wells, such as 6 wells, 12 wells, 24 wells, 48 wells, or 96 wells. The multi-well device can include two or more pairs of electrodes, wherein at least one well is positioned in between each pair of electrodes. In some embodiments, multi-well device can include 2-20 pairs of electrodes (e.g., 2-20 pairs, 2-10 pairs, or 4-8 pairs). In some embodiments, the multi-well device can include 2 pairs, 3 pairs, 4 pairs, 5 pairs, 6 pairs, 7 pairs, 8 pairs, 9 pairs, or more of electrodes. In some embodiments, 1-20 wells (e.g., 1-15 wells, 2-20 wells, 2-10 wells, or 4-8 wells) can be positioned in between each pair of electrodes. In some embodiments, 1 well, 2 wells, 3 wells, 4 wells, 5 wells, 6 wells, 7 wells, 8 wells, 9 wells, or more wells can be positioned in between each pair of electrodes. In some embodiments, the multi-well device can be in the form of a multi-well plate. In some embodiments, the multi-well plate is a 24-well plate having a 4×6 configuration. In the 4×6 configuration, there can be 6 pairs of electrodes, where 4 wells are positioned in between each pair of electrodes.

Each pair of electrodes can be used to apply electrical stimulations to all the wells in between the pair of electrodes. The operation of each pair of electrodes can be independent from the other pairs of electrodes, thereby permitting each pair of electrodes to have different stimulation parameters from the other pairs of electrodes.

Figures 2A, 2B, 2C:
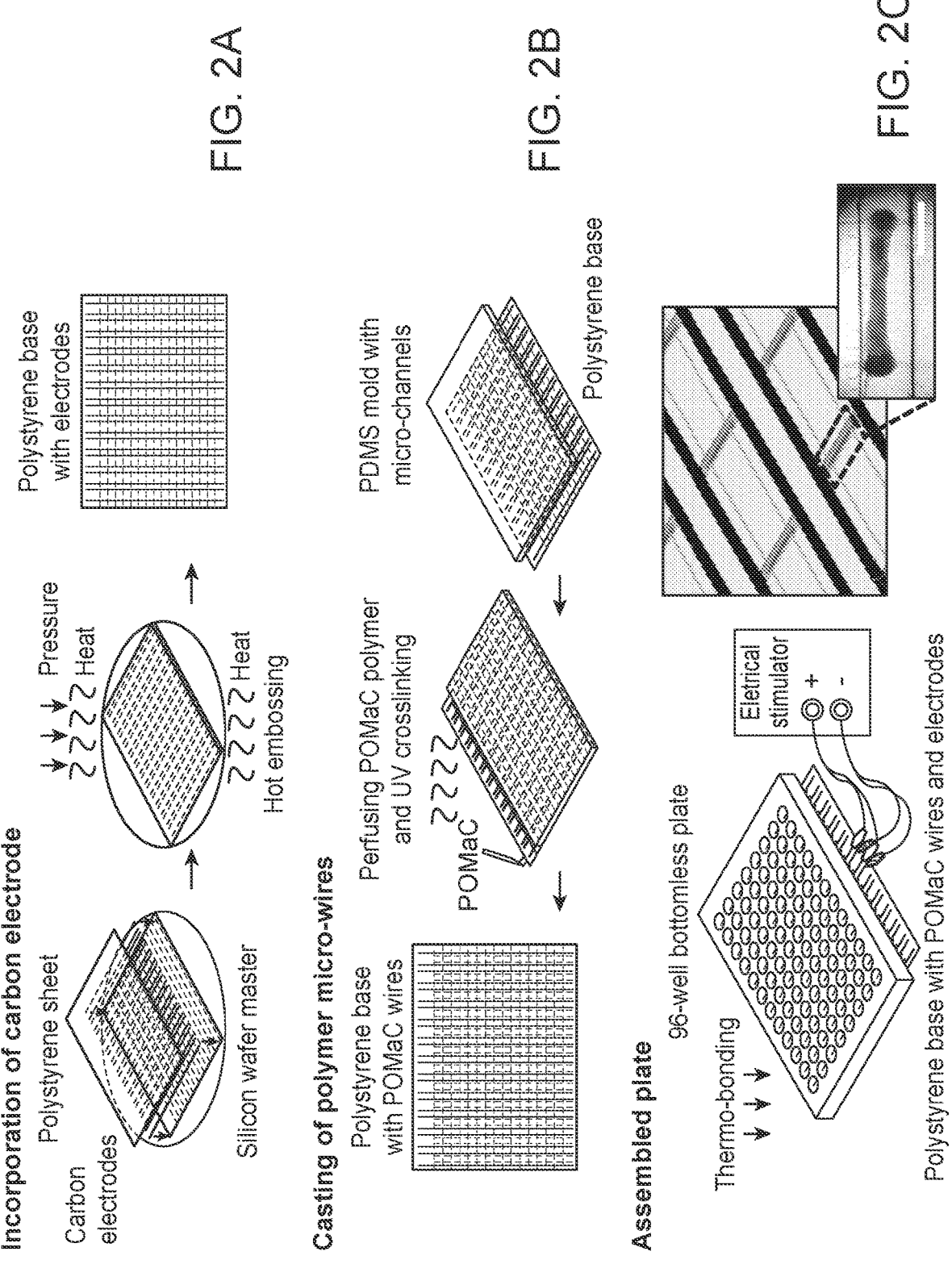
FIGS. 2A-2C show an overview of the schematics of the Biowire 96-well plate fabrication.

FIG. 2C shows a multi-well device having 96 wells on a single substrate. The multi-well device includes 12 pairs of electrodes, wherein each electrode is parallel or substantially parallel to the other electrodes. The black stripes indicate electrodes. 8 wells are positioned in between each pair of electrodes.

Hot embossing and injection molding techniques can be used to produce the devices described herein. In some embodiments, a custom multi-well plate can be first produced with embedded electrodes and channels, sensing elements can be laid down into the channels, and then a bottomless plate having a plurality of cell culture wells can be affixed on top of the multi-well plate. During affixation, the wells on the multi-well plate are aligned with the cell culture wells on the bottomless plate, such that each cell culture well contains a single well.

In one aspect, the present disclosure provides a system comprising: two or more devices described herein (e.g., multi-well devices); and a stimulator having two or more driver boards, wherein each driver board is configured to apply an electrical stimulation between each pair of electrodes of each device, thereby permitting the stimulator to independently control the application of the electrical stimulation between each pair of electrodes.

For in vitro tissue generation, the state of the art has the following shortcomings: (a) manual programing of electrical stimulation are required at all steps in the process; (b) electromechanical interfaces are handcrafted and manually connected; and (c) handcrafted systems are not designed for robustness, stability or ease of assembly/manufacturability.

In comparison, the system described herein provides a scalable, automated platform for the generation, manipulation, and maintenance of tissues in vitro. The system allows for every step of the primary workflow (e.g., seeding cells, maturation/stimulation and endpoint assay) to happen in the same location, without transferring the tissues from one chamber or petri dish to another. Each tissue can be a self-contained and isolated bioreactor. In some embodiments, when a multi-well bottomless plate is attached to a custom manufactured polystyrene plate, each microwell is effectively sealed off from the rest of the plate. During the culture process, media and nutrients can be applied on a tissue-by-tissue basis. Furthermore, the electrodes are already embedded into the plate, so there is no need to move the tissues in order to apply electrical stimulation for the maturation protocol. Given that each tissue is isolated, there is no need to separate them after maturation in order to apply any test compound for performing a test (e.g., a contractility assay). As a result, each tissue can be treated individually and independently of the other tissues on the plate (e.g., different doses of test compound).

In some embodiments, the stimulator can include at least 2 driver boards, at least 3 driver boards, at least 4 driver boards, at least 5 driver boards, or at least 6 driver boards. In some embodiments, the stimulator can include no more than 25 driver boards, no more than 20 driver boards, no more than 19 driver boards, no more than 18 driver boards, no more than 17 driver boards, no more than 16 driver boards, no more than 15 driver boards, or no more than 10 driver boards.

Combinations of the above-referenced ranges for the number of driver boards are also possible (e.g., at least 2 to no more than 25, at least 5 to no more than about 15, or at least 5 to no more than 10). In some embodiments, the stimulator can include about 10 driver boards.

In some embodiments, each driver board can include up to 6 channels. Each channel is an independently configurable output from a driver board (e.g., stimulation frequency). For example, a 24-well plate can be stimulated by 6 channels which are powered by a single driver board. As such, each driver board has the ability to control the stimulation parameters of each plate down to the column of wells, allowing one column on a given plate to have different parameters from the other columns on the same plate. The off-the-shelf stimulators are not capable of providing this level of control.

The number of driver boards can depend on the number of devices in the system, as each driver board can be used to control one device. For example, if there are 5 multi-well devices in the system, then there can be at least 5 driver boards; if there are 10 multi-well devices in the system, then there can be at least 10 driver boards.

Figure 17:
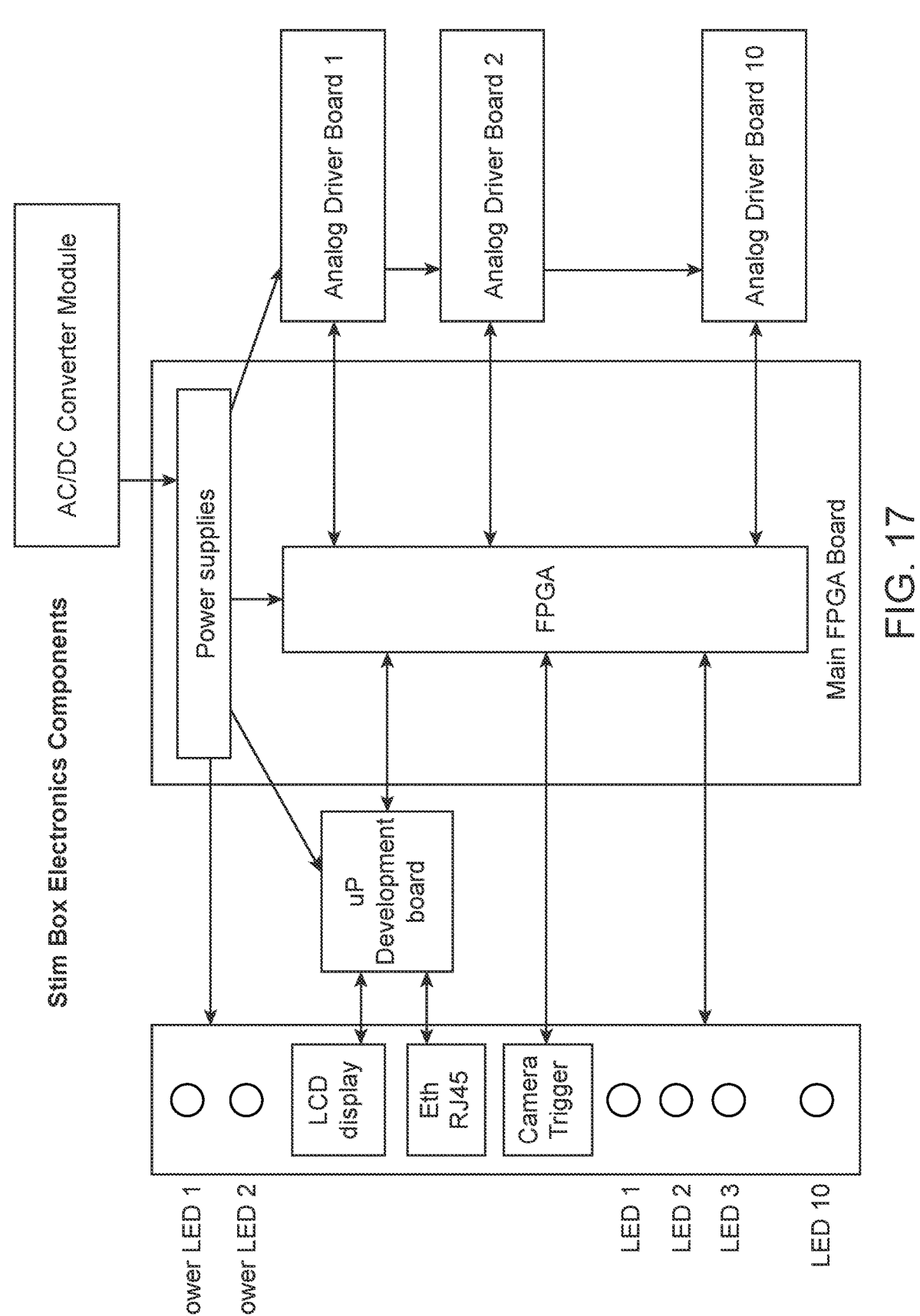
FIG. 17 is a schematic of the electronic components in a stimulator.

In some embodiments, the configuration of the electronic components in the stimulator is shown in FIG. 17.

The system permits an expandable number of channels, wherein each channel can be independently configurable. The advantages resulting from such independent configurability include, but are not limited to: (1) better thermal regulation and control; (2) permitting operation in an incubator without additional thermal control; (3) permitting automation of the stimulation parameters over maturation cycle; and (4) recordable stimulation history for each driver board.

In some embodiments, the system can further include an interface tray (e.g., a base plate) configured to couple the devices electrically to the stimulator. The interface tray can include a hinged lid for securing the devices and ensuring that the electrical contacts on the bottom of the devices are connected to the leads coming from the stimulator. When an operator in the lab needs to take a multi-well plate out of the incubator, he or she lifts the hinged lid and picks up the plate without having to unplug or disconnect any components, which makes the process easier and safer for the tissues.

In some embodiments, the system can further include an incubator configured to culture the cells and tissues grown in the devices. During the tissue maturation process, the devices must remain in an incubator at a constant temperature of about 37° C. while connected to the stimulator. In order to accomplish this, the incubator can include a custom incubator rack to house a plurality of the multi-well plates inside the incubator. In each space within the incubator rack, one of the incubator trays is fastened to the bottom of the rack to allow an operator to secure a multi-well plate in place. The connectivity between the stimulator, incubator rack, and interface trays can be managed by standard ribbon cabling and a custom printed circuit board (PCB) that is fastened to the back plane of the incubator rack.

The system can further include an imaging subsystem configured to produce an image of the sensing elements and/or tissue in each device. The imaging subsystem can include an optical microscope.

The system can further include a computing device coupled to the imaging subsystem and configured to analyze images and/or control the stimulator. The computing device can include a graphical user interface (GUI) for interfacing with and controlling the settings of the stimulator. The GUI allows the operator to check and adjust the stimulator settings from a remote location and set the stimulator to execute a pre-determined stimulation protocol automatically. In addition, the GUI can report errors back to the operator, such as open circuits, over/under voltage and network disconnections (e.g., between the controller and the stimulator). The stimulator GUI also allows the operator to label and track the maturation progress of the multi-well plates depending on the protocol settings or the project that the tissues are designated.

The stimulator can couple to the incubator and/or the imaging subsystem electrically.

Figure 12:
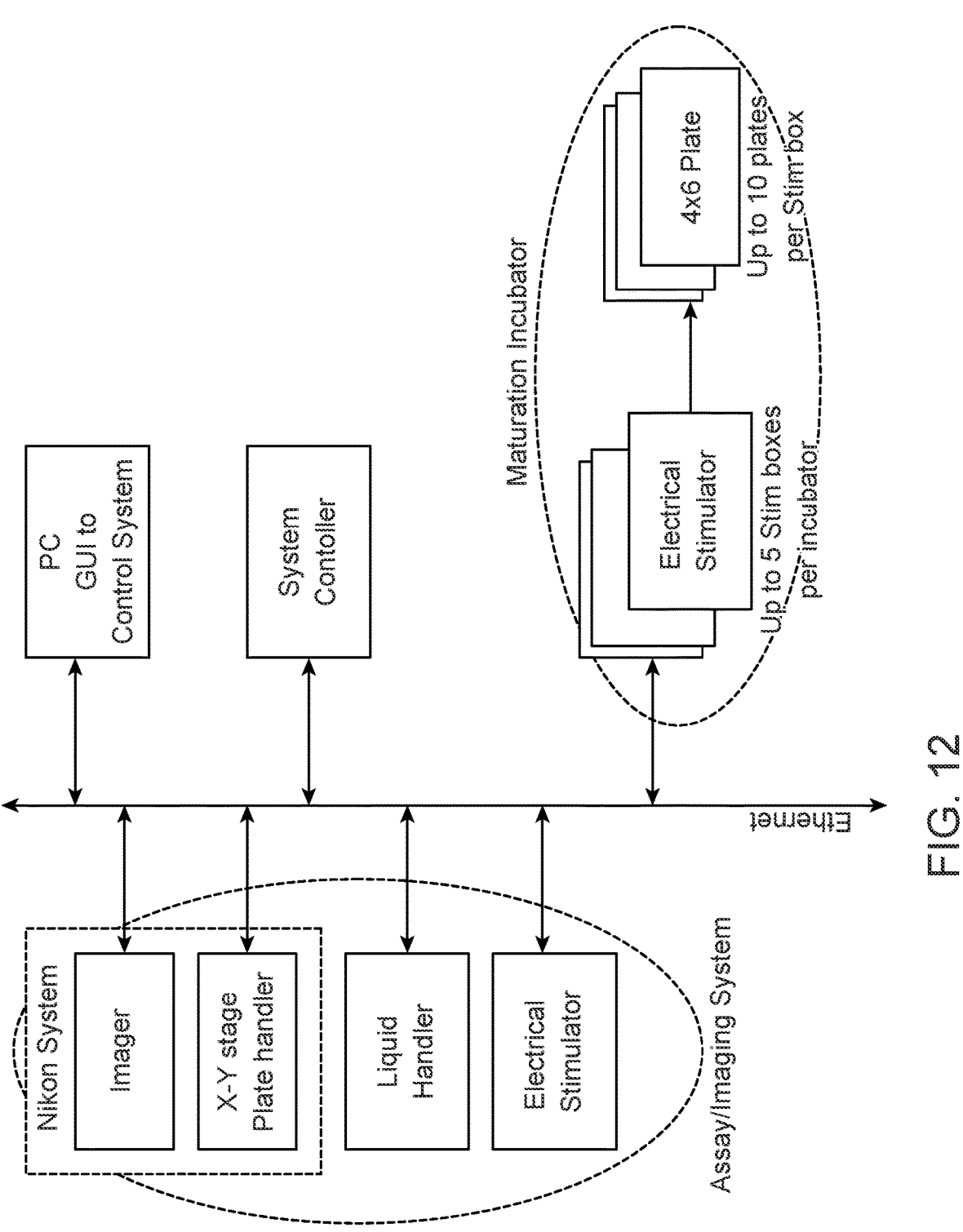
FIG. 12 is a high-level system architecture diagram in accordance with some embodiments of the present disclosure.

FIG. 12 is a high-level system architecture diagram in accordance with some embodiments of the present disclosure. As shown in FIG. 12, the system includes the following subsystems: (a) a maturation and incubation subsystem, (b) an assay and imaging subsystem, (c) a system controller, and (d) a computer that runs a GUI to set operating parameters. To accommodate scalability to beyond a single stimulator box, maturation incubator or assay/imager, each subsystem can be connected to the system via a wired or wireless network.

Once matured, the tissues are ready for drug testing. The testing can happen in the assay and imaging subsystem. In some embodiments, this subsystem can include a Nikon imager, X/Y stage controller to move the wells into the camera's field of view, a liquid handler to deposit the drug into each well, and the stimulator box. The goal of the system is to integrate these 4 components into a single physical platform. Once integrated, to automate the orchestration of the assay, the drug testing assays can be carried out on a column by column basis, one plate at a time. Each column represents each pair of embedded electrodes. The assay protocol also requires adjustment of the same stimulus pattern.

In some embodiments, the system can include two or more stimulators. A system controller can be used to manage all the stimulators. As the system expands, each of the stimulators can be assigned a unique identification by the system controller. The system controller is responsible for communicating the stimulus parameters for each column, for each plate, for each stimulator as parameterized on the GUI. It also monitors the status of each stimulator; periodically records and time stamps the operating parameters as well as checks on the health of the stimulator (checks for over-current alert conditions).

A browser-based GUI running on a networked computer can be the interface to the system controller. As long as that computer is on the same network, its physical location is irrelevant. The GUI computer can remotely access the system controller.

The adjustable parameters for the stimulator include, but are not limited to, pulse voltage, frequency of the pulse, and duration of the pulse. The stimulator is also responsible for monitoring the voltage and current applied to each pair of embedded electrodes. These measurements can be recorded periodically in a database. The electrical stimuli can be user adjustable through a GUI application running on a networked computer.

Figure 13:
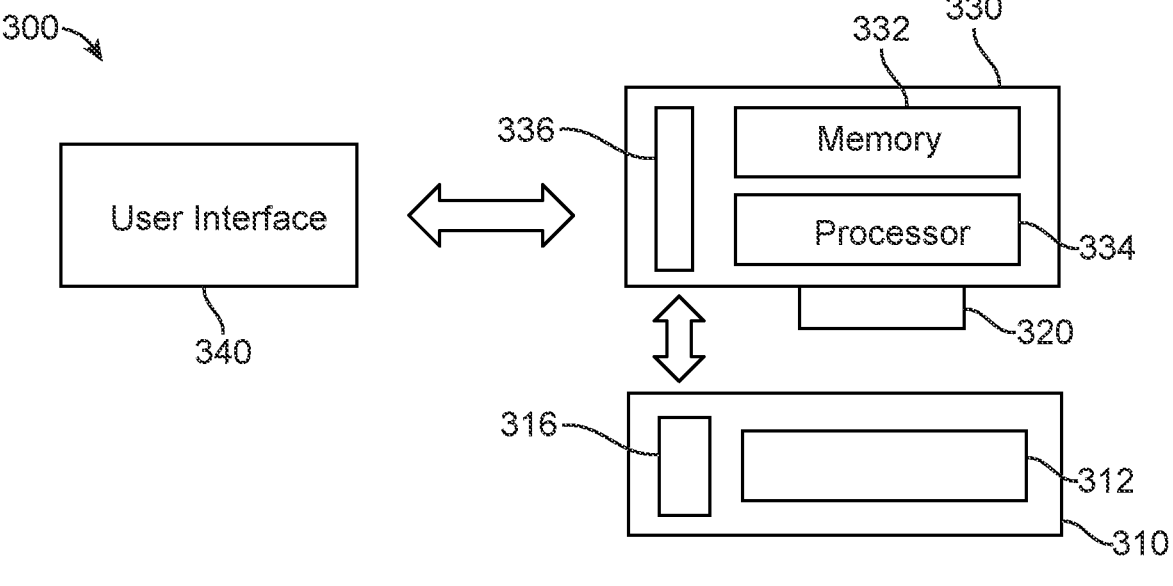
FIG. 13 shows a schematic of a system for implementing a 3D tissue culture, according to some embodiments of the present disclosure.

FIG. 13 shows a schematic of a system 300 for implementing a 3D tissue culture, according to an embodiment. The system 300 includes a tissue growth device 310 that further includes a growth well 312 and a control unit 316. In some embodiments, the growth well 312 can be substantially similar to the device 100 shown in FIG. 1 and described above. For example, the growth well 312 can include one or more embedded electrodes (not shown in FIG. 13) configured to stimulate the growth of tissues. In addition, the growth well 312 also includes one or more wires (not shown in FIG. 13) configured to sense the growth of the tissues. The control unit 316 is configured to control the operation of the growth well 312. In some embodiments, the control unit 316 can include a power source (not shown in FIG. 13) configured to provide power to the embedded electrode(s). In some embodiments, the control unit 316 is configured to receive power (e.g., electricity) from an external source. In some embodiments, the control unit 316 includes a signal generator (not shown in FIG. 13) configured to provide the electrical signals to the embedded electrodes. In addition, the control unit 316 can be configured to change one or more attributes of the electrical signals, such as, for example, the amplitude, frequency, repetition rate, and/or duration time, among others.

The system 300 also includes an imaging device 320 configured to monitor the growth of the tissues in the tissue growth device 310. In some embodiments, the imaging device 320 is configured to monitor the shape of sensing wires in the tissue growth device 310 to estimate the conditions of the tissue. The imaging device 320 can include any appropriate type of sensor(s), such as charge-coupled devices (CCDs), complementary metal-oxide-semiconductor (CMOS) devices, photodiodes, and/or phototransistors, among others. In some embodiments, the imaging device 320 includes optics, such as lenses, collimators, wave plates, polarizers, and/or filters, etc., to facilitate image acquisition. In some embodiments, the imaging device 320 includes a microscope.

A processing device 330 is operatively coupled to the imaging device 320 and configured to analyze the images acquired by the imaging device 320. The processing device 330 includes a memory 332, a processor 334, and a communication interface 336. The memory 332 can be, for example, random access memory (RAM), a memory buffer, a hard drive, a database, a read-only memory (ROM), an erasable programmable read-only memory (EPROM), an electrically erasable programmable read-only memory (EEPROM), and/or so forth. In some instances, the memory 332 includes a set of instructions or code used to perform one or more methods of data collection and/or data processing (including image classification) as described below with reference to FIGS. 14-16. The processor 334 can be any suitable processor such as, for example, a general purpose processor (GPP), a central processing unit (CPU), an accelerated processing unit (APU), a graphics processing unit (GPU), a network processor, a front-end processor, an application specific integrated circuit (ASIC), a field-programmable gate array (FPGA), and/or the like. Thus, the processor 334 can be configured to perform and/or execute a set of instructions, processes, modules, and/or code stored in the memory 332.

The communication interface 336 can be any suitable device that can place the processing in communication with other devices, such as a device implementing a user interface 340, the tissue growth device 310, and/or any other suitable device. In some embodiments, the communication interface 336 can include one or more wired and/or wireless interfaces, such as, for example, network interface cards (NIC), Ethernet interfaces, optical carrier (OC) interfaces, asynchronous transfer mode (ATM) interfaces, and/or wireless interfaces (e.g., a WiFi® radio, a Bluetooth® radio, a near-field communication (NFC) radio, and/or the like).

The user interface 340 is configured to allow a user to interact with the rest of the system 300. In some embodiments, the user interface 340 is configured to display available protocols that can be implemented by the system 300 and allows a user to select one or more protocols to be implemented. In some embodiments, the user interface 340 is configured to display the analysis results generated by the processing device 330. In these embodiments, the analysis results can include, for example, the images acquired by the imaging device 320 (with or without processing), the growth conditions of tissues in the tissue growth device 310, and potential defects in the tissues, among others. In some embodiments, the user interface 340 includes a graphic user interface (GUI) associated with a webpage, PC application, mobile application, and/or the like. In some embodiments, the user interface 340 can include a touch screen configured to receive a haptic user input. In some embodiments, the user interface 340 can be implemented by any suitable compute device such as, for example, a desktop, a laptop, a personal computer, a server, a mainframe computer, a smartphone, a tablet, a wearable device, and/or the like.

FIG. 14 is a flowchart illustrating a method 400 for image processing, according to an embodiment. In some embodiments, the method 400 can be implemented by the processor 334 (e.g., by executing instructions stored in the memory 332). The method 400 includes, at 410, receiving an image (also referred to as an input image) of a tissue growing around a wire within a well from cells seeded within the well. In some embodiments, the image is acquired by the imaging device 320 in the system 300 of FIG. 13.

The method 400 also includes, at 420, defining a first binary image based on comparing each pixel from a plurality of pixels in the image to a pixel threshold. In some embodiments, pixel values equal to or greater than the pixel threshold are set to 1, and pixel values less than the pixel threshold are set to 0 to generate the first binary image. In some embodiments, the definition can be reversed, i.e., pixel values equal to or less than the pixel threshold are set to 1, and pixel values greater than the pixel threshold are set to 0. In some embodiments, the first binary image is defined using Otsu's method (see more details with reference to FIGS. 15A-15B below).

At 430 of the method 400, a first edge and a second edge of the wire within the first binary image are detected to define a second binary image representing the first edge and the second edge. In some embodiments, the first edge and the second edge are detected based on the gradient of pixels in the first binary image. In some embodiments, the first edge and the second edge are detected using a Sobel operator (see more details with reference to FIGS. 15G and 15H below).

At 440 of the method 400, a midpoint between the first edge and the second edge is calculated for each row in the second binary image, thereby resulting in a set of midpoints. In some embodiments, the midpoint of an mth row in the second binary image is characterized by two-dimensional (2D) coordinates $(x_m, y_m)$, and $x_m=(x_1+x_2)/2$, where $(x_1, y_m)$ is the coordinate of the pixel on the first edge and $(x_2, y_m)$ is the coordinate of the pixel on the second edge. In some embodiments, the wire in the image (including the first edge and the second edge) is along the x direction. In these embodiments, the midpoint can be calculated for each column in the second binary image.

The method 400 also includes, at 450, calculating a quadratic equation that fits the set of midpoints based on a polynomial regression of the set of midpoints. In some embodiments, the quadratic equation represents a contour (or shape) of the wire in the input image. At 460 of the method 400, a point of deflection in the wire is identified based on the quadratic equation.

In some embodiments, the well includes a set of electrodes configured to apply an electrical stimulation to the tissue according to a set of stimulation parameters. In these embodiments, the method 400 further includes adjusting a set of values for the set of stimulation parameters based on the point of deflection in the wire (i.e., identified at 460) meeting a predetermined criterion to define an updated set of values for the set of stimulation parameters. Then a stimulation signal is sent to the set of electrodes to apply the electrical stimulation to the tissue according to the updated set of values for the set of stimulation parameters. In other words, the deflection point identified at 460 can be used (e.g., by the processor 334) to derive the growth conditions of the tissue.

In some embodiments, the method 400 also includes removing artifact pixels from the first binary image using an opening operator prior to detecting the first edge and the second edge of the wire within the first binary image (see more details with reference to FIGS. 15C and 15D below). In some embodiments, the method 400 also includes smoothing the first binary image using a closing operator prior to detecting the first edge and the second edge of the wire within the first binary image (see more details with reference to FIGS. 15E and 15F below).

In some embodiments, the method 400 further includes completing, prior to calculating the midpoint at 440, a portion of the first edge or a portion of the second edge not included within the second binary image. In this manner, each row in the second binary image includes a portion of the first edge and a portion of the second edge (see more details with reference to FIGS. 15K and 15L below).

In some embodiments, the deflection point identified at 460 can be used to calculate the amount of contractile force exerted on the wire by the tissue. In some embodiments, the deflection point identified at 460 can be used to calculate the passive tension on the wire. The contractile force and/or the passive tension can indicate the growth condition of the tissue (e.g., degree of maturity) and therefore can be used to form a feedback control loop (see more details below with reference to FIG. 16).

FIGS. 15A-15M illustrate a method of wire tracking (also referred to as the wire tracking method), according to some embodiments. In general, the wire tracking method is configured to identify the edges of the wire sensor in each input image to compute a skeleton structure, which is represented by a set of 2D coordinates $(x_i, y_i)$, where i=1, 2, 3, . . . , N, and N is a positive integer. The 2D coordinates of the skeleton are then fitted to a second degree polynomial equation (e.g., using least square fitting). Without loss of generality, a second degree polynomial equation (also referred to as a parabola) can be written as:

$$y=ax^2+bx+c \tag{1}$$

In some embodiments, the wire tracking method includes a bit conversion step, in which the input images are converted into 8-bit images (i.e., images having a grayscale from 0 to 255). In some instances, the data value of each pixel in the input images is in the form of a 16-bit integer format. In these instances, it can be helpful to convert these images into 8-bit images to facilitate subsequent processing.

Direct conversion of 16-bit to 8-bit values may result in losing certain data and may also affect the threshold value when certain frames have a slight brightness gradient. The effect on the threshold, in turn, may lead to baseline spikes. To address this issue, a normalization step can be performed when converting input images from 16-bit to 8-bit. More specifically, at this normalization step, a range minimum (i.e., the minimal pixel value) and range maximum (i.e., the maximal pixel value) are identified for each frame. Then each pixel value in the frame is adjusted according to contrast stretching, e.g., the range minimum is stretched to 0 and the range maximum is stretched to 256. Intermediate values between the minimum and maximum are stretched proportionate to where they lie in the range from minimum to maximum. The 8-bit input images are then converted into binary images via thresholding. In some embodiments, the pixel value of each pixel in the input images is compared to a threshold value. In the event that the pixel value is equal to or greater than the threshold value, the pixel value is set to 1; otherwise, the pixel value is set to 0. In some embodiments, the definition can be inverse, i.e., the pixel value is set to 0 if equal to or greater than the threshold value and is set to 1 if less than the threshold value. In some embodiments, the 8-bit images can be inverted before the thresholding process, i.e., the wire section is set to black and the background section is set to white.

In some embodiments, the binary images are generated using the Otsu's method. Without being bound by any particular theory or mode of operation, the Otsu's method is an adaptive thresholding method for binarization in image processing. By going through the possible threshold values (e.g., from 0 to 255), the Otsu's method can find an optimal and/or desirable threshold value of input image. Unlike other thresholding methods which use a fixed threshold value, the Otsu's method computes the threshold based on the input image. This means that the Otsu's method will have different threshold values computed for different images.

In some embodiments, the optimal and/or desirable threshold value can be determined by minimizing the within-class variance $V_w$ or maximizing the between-class variance $V_b$. For a given threshold value T, pixels in an input image can be divided into two classes, including class 1 for pixels having a pixel value equal to or less than T and class 2 for pixels having a pixel value greater than T. In some instances, class 1 and class 2 are referred to as the background and foreground, respectively, of the input image. The within-class variance $V_w$ for each class can be calculated as:

$$\sigma^2 = \Sigma_{i=0}^{N}(X_i-\mu)^2)/N \qquad (2)$$

where $\mu$ is the mean value of pixel values in a given class, N is the number of pixels in the given class, and Xi is the pixel value of each pixel in the given image.

The between-class variance $V_b$ is characterizing the variance between the two classes. In some embodiments, the between-class variance $V_b$ can be calculated as $V_b=V_t-V_w$, where $V_t$ is the total variance, i.e., the variance of all pixels in the input image. For a given image, Vt is usually a constant. Therefore, minimizing $V_w$ usually results in the maximal $V_b$ at the same time.

Figures 15A, 15B, 15C, 15D:
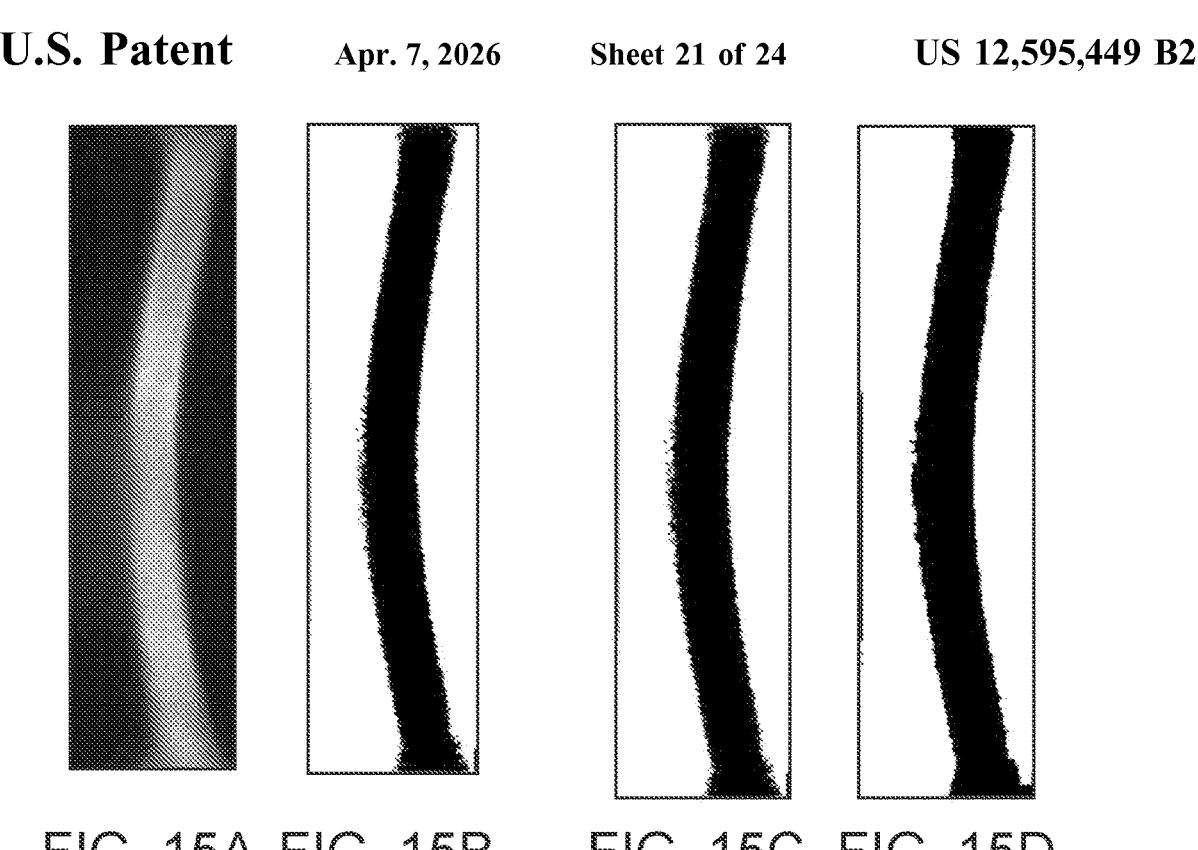
FIGS. 15A-15M illustrate various stages of a method of wire tracking, according to some embodiments of the present disclosure.

FIG. 15A shows an example input image before thresholding. FIG. 15B shows the input image after thresholding using the Otsu's method. In addition, the input image of FIG. 15A is inverted before thresholding. As can be seen in the binary image in FIG. 15B, the wire section is set as the background (i.e., black) and the rest of the image is set as the foreground (i.e., white).

The binary images generated after thresholding are then subject to one or more morphological operations. The morphological operations can include two operations: erosion and dilation. Both operations can have two inputs: (1) an image to be processed; and (2) a structuring element (also known as a kernel). Each of the two inputs is represented by a set of coordinates.

More specifically, the erosion operation on a binary image can be performed as follows. Denote X as the set of Euclidean coordinates corresponding to the input binary image and denote K as the set of coordinates corresponding to the structuring element. In addition, denote Kx as the translation of K so that the origin of the structuring element is at x. With these notions, the erosion of X by K is the set of all points x such that Kx is a subset of X.

To compute the erosion of a binary input image by this structuring element K, one can consider each of the foreground pixels in the input image in turn. For each foreground pixel (also referred to as the input pixel), the structuring element is superimposed on top of the input image such that the origin of the structuring element coincides with the input pixel coordinates. If for every pixel in the structuring element, the corresponding pixel in the binary image underneath is a foreground pixel, then the input pixel is left as it is. If any of the corresponding pixels in the image are background, however, the input pixel is also set to background value.

In some embodiments, the structuring element is 3×3, and the effect of erosion operation using this structuring element is to remove any foreground pixel that is not completely surrounded by other white pixels (assuming 8-connectedness). These pixels can lie at the edges of white regions, and so the practical effect of erosion is that foreground regions shrink and holes inside a region grow.

The dilation operation on a binary image can be performed as follows. First, denote X as the set of Euclidean coordinates corresponding to the input binary image, K as the set of coordinates for the structuring element, and Kx as the translation of K so that its origin is at x. Then the dilation of X by K is the set of all points x such that the intersection of Kx with X is non-empty. More specifically, to compute the dilation of a binary input image by the structuring element K, one can consider each of the background pixels in the input image in turn. For each background pixel (also referred to as the input pixel), the structuring element is superimposed on top of the input image such that the origin of the structuring element coincides with the input pixel position. If at least one pixel in the structuring element coincides with a foreground pixel in the image underneath, then the input pixel is set to the foreground value. If all the corresponding pixels in the image are background, however, the input pixel is left at the background value.

In some embodiments, the structuring element is 3×3, and the effect of a dilation operation using this structuring element is to set to the foreground color any background pixels that have a neighboring foreground pixel (assuming 8-connectedness). These pixels can lie at the edges of white regions, and so the practical effect of a dilation operation is that foreground regions grow and holes inside a region shrink.

In the wire tracking method described herein, the binary images generated by thresholding are processed with opening and closing operations. Morphological opening and closing are essentially the erosion and dilation operators applied in varying order. Without being bound by any particular theory or mode of operation, an opening is defined as an erosion followed by a dilation using the same structuring element for both operations, and a closing operation is defined as a dilation followed by an erosion using the same structuring element for both operations.

The basic effect of an opening is to remove some of the foreground (i.e., bright) pixels from the edges of regions of foreground pixels. But opening is typically less destructive than erosion. A closing operation tends to enlarge the boundaries of foreground (i.e., bright) regions in an image (and shrink background color holes in such regions), but it is less destructive than dilation in general.

Figures 15E, 15F, 15G, 15H:
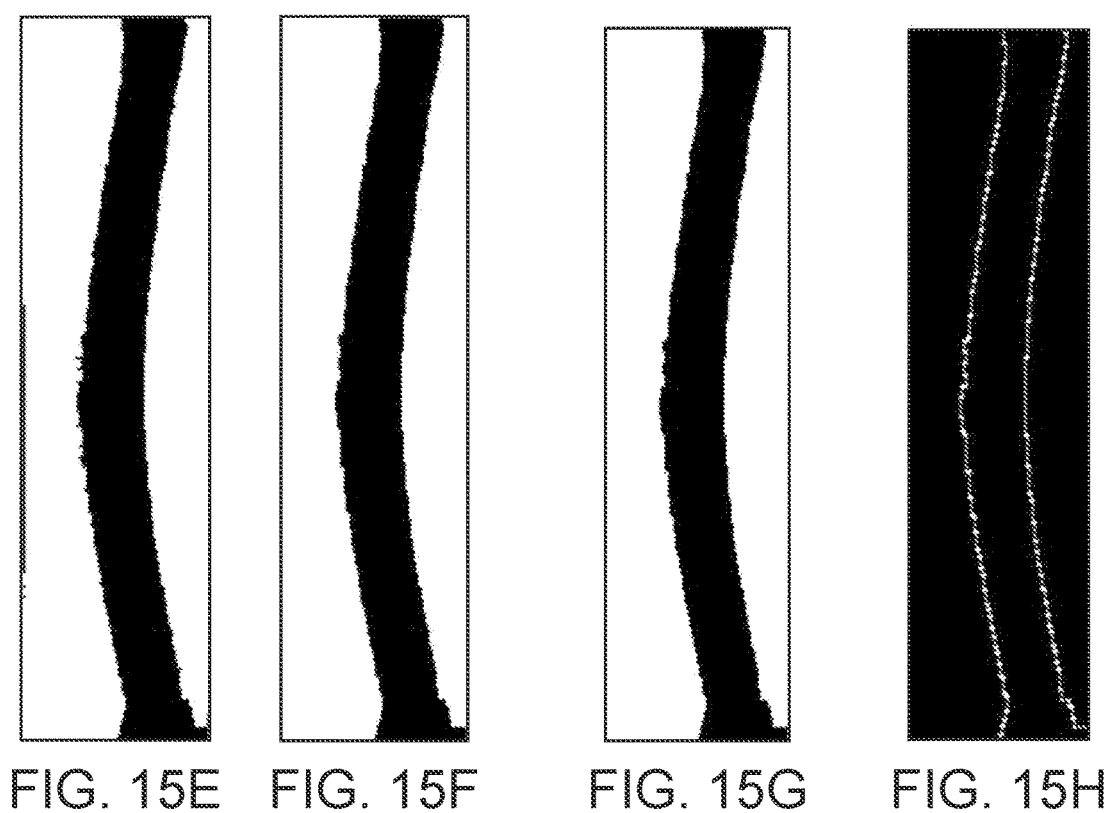

FIG. 15C shows a binary image generated after thresholding, and FIG. 15D shows a binary image generated after performing an opening operation on the binary image shown in FIG. 15C. FIG. 15E shows a binary image before a closing operation, and FIG. 15F shows a binary image generated after performing the closing operation on the binary image shown in FIG. 15E. In FIGS. 15C-15F, the structuring element is 5×5. In some embodiments, the closing operation is performed after the opening operation. In some embodiments, the order can be reversed, i.e., the opening operation is performed after the closing operation.

As can be seen in FIG. 15C-15F, the morphological operations of opening and closing help in clearing out and/or reducing the artifacts that may obstruct the edges of the wire. The opening operator is applied to remove unwanted stray pixels and to clean the edges of the wire. The closing operator, on the other hand, can fill the empty space and clear unwanted lines (e.g., as seen on the left side of the input image versus the output image in FIGS. 15E-15F).

The wire tracking method also includes an edge detection step, where the edges of the wire in the input image are identified. The input image in this step can be, for example, the image after the morphological operations described above. In some embodiments, the edge detection is performed using a Sobel operator that is configured to calculate gradients of pixel values in both the x and y directions. The Sobel operator convolves kernels with the input image to calculate approximations of the derivatives to detect the edges.

More specifically, a first kernel $G_x$ can be convolved with the input image from left to right to obtain the gradient in the first direction (e.g., the x direction). Without loss of generality, the first kernel can be written as, for example:

$$G_x = \begin{bmatrix} +1 & 0 & -1 \\ +2 & 0 & -2 \\ +1 & 0 & -1 \end{bmatrix} \tag{3}$$

A second kernel $G_y$ can be convolved with the input image from top to bottom to obtain the gradient in the second direction (e.g., they direction). Without loss of generality, the second kernel can be written as, for example:

$$G_y = \begin{bmatrix} +1 & +2 & +1 \\ 0 & 0 & 0 \\ -1 & -2 & -1 \end{bmatrix} \tag{4}$$

The above two convolution steps generate two vectors representing the gradient of the image in x and y directions. Accordingly, the magnitude of the gradient at each pixel in the input image can be calculated as:

$$G=\sqrt{(G_x)^2+(G_y)^2} \tag{5}$$

FIG. 15G shows a binary image after the opening and closing operation described above, and FIG. 15H shows a binary image after edge detection using the Sobel's operator. The image after edge detection (FIG. 15H) is also referred to as the edge detected image. As can be seen in FIG. 15H, the two edges of the wire (i.e., the right edge and the left edge) are detected and illustrated as while lines.

Figures 15I, 15J, 15K, 15L:
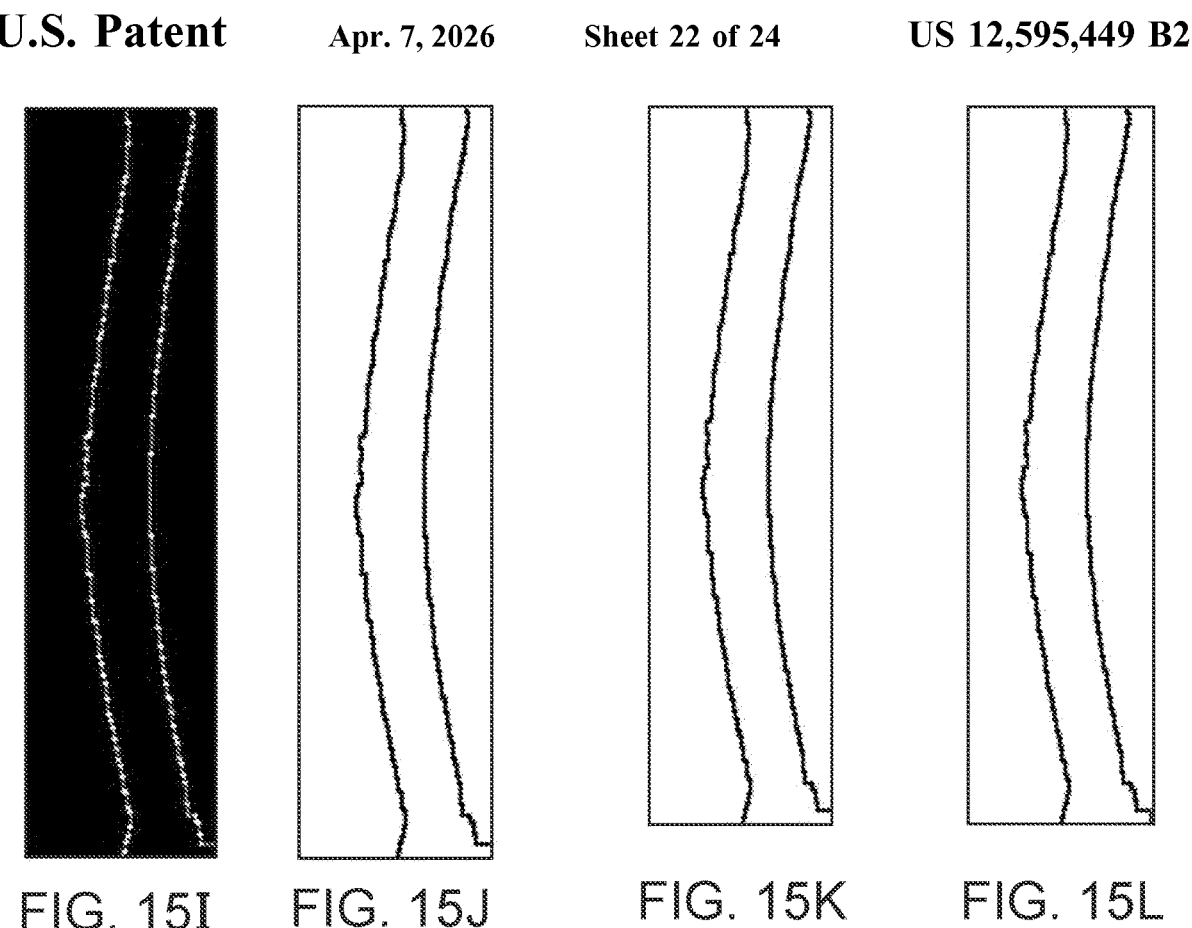

In some embodiments, the edge detected image (e.g., the image shown in FIG. 15H) is processed with another thresholding in the wire tracking method to generate another binary image. In some embodiments, the thresholding at this step can be performed using the Otsu's method as described above. FIG. 15I shows an edge detected image and FIG. 15J shows a binary image generated after thresholding using the Otsu's method.

In some embodiments, the edge detected image is further processed with edge filling (e.g., after the thresholding). In some instances, the wire edges are cropped in the edge detected image, and the edge filling is configured to fill in the empty edges (e.g., at the top and bottom portions of the detected edges). In some instances, the cropping of wire edges in the edge detected images can be attributed to the kernel used in the edge detection process, and the edges that are cropped out of the image frame are not detected. Accordingly, the left and right edges are not completely computed for each row.

The edge filling technique described herein traverses from the center row in the edge detected image upwards and downwards until it detects a row where either the right edge point or the left edge point is the last or the first column of the image (i.e., the wire edge point is also on the image edge). From there on, the rows above are filled with a right or left edge as the last or the first column.

FIG. 15K shows an edge detected image after thresholding and FIG. 15L shows an image obtained by perform edge filling on the image shown in FIG. 15K. The image after edge filling is also referred to as the edge filled image. As can be seen in FIG. 15K, the lower portion of the right edge of the wire is filled along the right edge of the image.

Figure 15M:
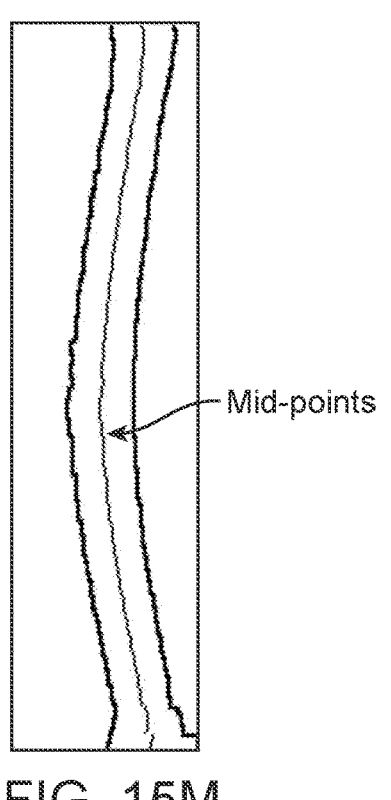

The next step in the wire tracking method includes mid-point calculation. At this step, the mid-point of the wire is calculated for each row in the edge filled image. The mid-point can be calculated by taking an average of a first coordinate representing the left edge and a second coordinate representing the right edge. FIG. 15M shows an example image illustrating a set of computed mid-points.

Once the mid-points are computed, these mid-points can then be used as inputs for a polynomial regression to produce a quadratic equation that best fits the mid-points. In statistics, polynomial regression is a form of regression analysis in which the relationship between an independent variable x and a dependent variable y is modelled as an nth degree polynomial in x. More specifically, the regression method described herein fits the second-degree polynomial equation using the least squares method. The mid-points calculated above are represented by the corresponding x and y co-ordinates. The co-ordinates are essentially the row and the column numbers. These sets of x and y values are used to compute an equation using the polynomial regression method.

Without loss of generality, the regression method can be described by the following equations, for example:

$$y_i=ax_i^2+bx_i+c(i=1,2,\ldots,\text{number of image rows}) \tag{6}$$

where, $x_i$ and $y_i$ are the mid-point co-ordinates computed for each image frame.

Equation (6) can be written in a matrix form as follows:

$$\begin{bmatrix} y_1 \\ y_2 \\ \vdots \\ y_n \end{bmatrix} = \begin{bmatrix} 1 & x_1 & x_1^2 \\ 1 & x_2 & x_2^2 \\ \vdots & \vdots & \vdots \\ 1 & x_n & x_n^2 \end{bmatrix} \cdot \begin{bmatrix} a \\ b \\ c \end{bmatrix} \tag{7}$$

Or more concisely:

$$Y=X\cdot A \tag{8}$$

where Y is a vector having elements $(y_1, y_2, \ldots, y_n)$, X is a matrix including computed mid-points $x_i$, and A is a vector including fitting parameters a, b, and c.

Solving the Equation (8) can obtain:

$$A = (X^T X)^{-1} \cdot X^T \cdot Y \qquad (9)$$

Equation (9) is performed for each input image frame to produce a quadratic equation for each frame. Accordingly, the fitting parameters (also referred to as fitting coefficients) are calculated for each image frame.

The fitting coefficients of the quadratic equations from the previous step are used to detect the maximum point of deflection or displacement of the parabolic curve. In some embodiments, the deflection point can be detected by taking a derivative of the equation to find maxima at $x_M$. Then substituting that value of x with $x_M$ in Equation (6) to obtain the y coordinate, i.e., $y_M$. This $y_M$ value is used in the plot to represent the displacement of the wire.

The deflection point identified above can be used to calculate the force imposed on the sensing wire. In general, quantification of force transients involves accurate identification of the location of each transient within a force recording. In some embodiments, a peak analysis method can be used to identify force transients by aligning a theoretical force trace (also referred to as a simulated force trace) with the actual force trace. Thea actual force trace is a graph that results from plotting changes in the measured force over time. Contractions in the tissue appear as peaks and valleys in the resulting trace as the force increases and decreases over time, repeatedly. The theoretical force trace is generated with artificial transients at known intervals or a known frequency. The peak analysis method has the advantage of identifying transient peaks in recordings with low signal-to-noise ratio (SNR) or in recordings where amplitude of the force transient is diminished in response to compounds resulting in very small force transient recordings.

The actual force trace is then fit to a polynomial function to reduce the noise in the raw force transient trace and parameters of contraction are calculated from the polynomial function. These parameters of contract include, for example, transient amplitude, transient duration, time to peak of transient, time from peak of transient, maximal slope of force generation, and maximal slope of force deception, among others.

FIG. 16 is a flowchart illustrating a method 500 of operating a tissue culture, according to an embodiment. In some embodiments, the method 500 can be performed by the processor 334 in the system 300 illustrated in FIG. 13. In these embodiments, the memory 332 in the system 300 includes a non-transitory processor-readable medium configured to store processor-executable code. The processor 334, upon execution of the processor-executable code, performs the method 500.

The method 500 includes, at 510, receiving a set of measurements from at least one sensing element associated with a well (e.g., the well 312 in FIG. 13) configured for growing a tissue from cells seeded within the well. The well includes a set of electrodes configured to apply an electrical stimulation to the tissue according to a set of stimulation parameters. The method 500 also includes, at 520, identifying an amount to change a set of values for the set of stimulation parameters based on a comparison of the set of measurements to a set of predetermined criteria associated with the tissue. The amount to change the set of stimulation parameters is then used to adjust the set of values so as to define an updated set of values for the set of stimulation parameters at 530. A stimulation signal is then sent to the set of electrodes, at 540, to apply the electrical stimulation to the tissue according to the updated set of values for the set of stimulation parameters.

In some embodiments, the set of stimulation parameters includes at least one of stimulation voltage, stimulation frequency, and/or stimulation time. In some embodiments, the stimulation signal can be sent by the processor 334 to the control unit 316 of the tissue growth device 310 via the communication interface 336. The control unit 316 is then configured to implement the stimulation signal by sending an electrical signal to the electrodes characterized by the stimulation parameters specified in the stimulation signal. In other words, the stimulation signal sent by the processor 334 functions as an instruction to the control unit 316, which then controls the operation of the electrodes based on the instruction.

In some embodiments, the sensing element includes at least two elastic sensing elements (e.g., sensing wires) disposed across the well such that there is a gap between the sensing elements and a bottom of the well. In these embodiments, the growth of the tissue within the well can impose a force to the elastic sensing elements, thereby causing a change of shape in the elastic sensing element. In some embodiments, the processor 334 in the system 300 is configured to analyze the shape (or the change of shape) of the elastic sensing element so as to determine the growth conditions of the tissue within the well. In response to the determined growth condition, the processor 334 is configured to determine the amount to change the set of stimulation parameters.

In some embodiments, the initial set of values for the set of stimulation parameters is selected based on a predetermined stimulation protocol. In some embodiments, the user interface 340 is configured to present the predetermined stimulation protocol, among multiple available stimulation protocols, to a user, and the user can select one stimulation protocol as the predetermined stimulation protocol.

In some embodiments, the predetermined criteria associated with the tissue includes a maturity criterion and/or an excitation criterion for the tissue. In response to the set of measurements meeting the maturity criterion and/or an excitation criterion, the stimulation voltage can be reduced accordingly (e.g., by the processor 334). In response to the set of measurements not meeting the maturity criterion and/or an excitation criterion, the stimulation voltage can be increased accordingly (e.g., by the processor 334). In some embodiments, the set of measurements include the maturity condition and/or an excitation criterion of the tissue derived from images of the sensing element. For example, the processing of the data from the sensing wires may show that deflection of the wires is not large enough (e.g., less than a threshold deflection amount), thereby indicating that the tissue is not as mature as expected. In this event, the stimulation voltage can be increased.

In some embodiments, the set of measurements can be provided by additional sensors, such as voltage sensors that are configured to measure the voltage applied to the embedded electrodes. In response to the measured voltage less than a threshold voltage (e.g., specified in a protocol), the processor can send an instruction to the control unit 316 to increase the voltage. Any other operation parameters of the tissue growth device 310 can also be adjusted in a similar way.

In some embodiments, the method 500 further includes periodically receiving (e.g., at the processor 334) an instance of the set of measurements and storing the instance of the set of measurements in a memory (e.g., the memory 332). In these embodiments, the growth history of the tissue in the well can be recorded. In some embodiments, the set of measurements also includes the operation parameters of the tissue growth device 310, such as the frequency and voltage applied to the electrodes. In some embodiments, the set of measurements is stored in the memory in, for example, comma-separated values (CSV) format or any other suitable format for later analysis and troubleshooting in the event that a problem with the tissues is detected.

In some embodiments, the method 500 can be performed by the processor without human intervention for a preset period of time (e.g., about several days to several weeks). In these embodiments, the user interface 340 can present the user with several available protocols and the user selects one for implementation. Once the user selects the protocol, the system 300 can be configured to implement the protocol (and update any stimulation parameters based on feedback as described in method 500) without further human intervention. In some embodiments, the user interface 340, upon completion of the implementation of the protocol, can be configured to display the growth result. The growth result can include, for example, images of the tissues, images of the sensing wires, maturity conditions and/or excitation conditions of the tissues obtained from analyzing the sensing wires, among others.

In some embodiments, the set of measurements can be used to assess the quality of the tissue growth. Such assessment can include, for example, detecting one or more issues in the tissue growth. In some embodiments, the processor 334 can be configured to detect one or more issues (e.g., contamination, debris, holes in the tissue, etc.) in the tissue growth based on the set of measurement via machine learning. In these embodiments, the processor 334 can be configured to implement, for example, an artificial neural network that is configured for image classification. The image classification can classify an input image into one of several categories, each of which represents a common issue in tissue growth. The input image can be an image of the tissue, an image of the tissue where it wraps around the sensing elements, or any combination thereof.

In some embodiments, in response to detecting an issue in tissue growth (e.g., by the machine learning model), the processor 334 is further configured to take remedial actions, such as changing the stimulation parameters. In some embodiments, in response to detecting an issue in tissue growth, the processor 334 is further configured to generate an alert signal. In some embodiments, the processor 334 is configured to send the alert signal to the user (e.g., via the communication interface 336). The alert signal can include, for example, a text message, an email, a voicemail, or a real-time call. In some embodiments, each category of common issues is assigned an error code, and the alert signal sent to the user includes the error code.

Referring back to FIG. 13, in some embodiments, the system 300 (or the processor 334) can be configured to perform end-to-end data analysis. In these embodiments, raw data (e.g., raw images of the sensing wires) is first sent to the processor 334 for wire tracking to generate force values over time based on the movement of the wire. For example, the processor 334 can be configured to implement the method described with reference to FIG. 14 and FIGS. 15A-15M. The force values are then used for peak analysis, which is configured to generate quantitative readouts, such as peak amplitudes, time-to-peak, etc. The quantitative readouts are then used to plot graphical representations. The graphical representations can be force traces, changes in maximum force over time, comparisons of time-to-peak before and after drug treatment, etc. In the end-to-end analysis, the above actions can be performed by the processor 334 (or other processors) without human intervention. For example, a user can select a protocol to be implemented by the system 300 and then receive the graphical representations upon completion of the protocol. In some embodiments, the graphical representations can be displayed on the user interface 340. In some embodiments, the graphical representations can be sent to the user via a network (wired or wireless). For example, the graphical representations can be sent to a smartphone or a computer associated with the user.

In some embodiments, the system 300 (or the processor 334) can be configured to implement a scheduler for operating the issue growth device 310. In some embodiments, the processor 334 can include an FPGA to implement the scheduler via Verilog or other appropriate language. In some embodiments, the operator can use the user interface 340 to set the pulse interval for the system 300. The user interface 340 is configured to send pulse interval information to the scheduler, which in turn is configured to generate a time table to determine precisely when a particular well in the tissue growth device 310 will receive a pulse (e.g., for stimulation). Therefore, the scheduler can be used to provide precise stimulation timing on average, with short term deviation to account for serial well stimulation.

Some embodiments described herein relate to methods. It should be understood that such methods can be computer implemented methods (e.g., instructions stored in memory and executed on processors). Where methods described above indicate certain events occurring in certain order, the ordering of certain events can be modified. Additionally, certain of the events can be performed repeatedly, concurrently in a parallel process when possible, as well as performed sequentially as described above. Furthermore, certain embodiments can omit one or more described events.

Some embodiments described herein relate to computer-readable medium. A computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, PLDs, ROM and RAM devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using Python, R, Java, JavaScript, C++, or other programming languages and development tools. Additional examples of computer code include, but are not limited to, control signals, encrypted code, and compressed code.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." Any ranges cited herein are inclusive.

The terms "substantially", "approximately," and "about" used throughout this Specification and the claims generally mean plus or minus 10% of the value stated, e.g., about 100 would include 90 to 110.

As used herein, the term "POMaC" refers to poly(octamethylene maleate (anhydride) citrate) (POMaC) or the POMaC prepolymer which comprises a mixture of 1,8-octandiol, citrate acid, and maleic anhydride. Reference can be made to Tran et al., "Synthesis and characterization of a biodegradable elastomer featuring a dual crosslinking mechanism," Soft Matter, Jan. 1, 2010; 6(11): 2449-2461, which is incorporated herein by reference in its entirety.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

EXAMPLES

Example 1

Here, innovative multimaterial processing into a scalable and functional plat-form is proposed in the format of a 96-well plate. Three classes of materials are integrated into the platform. An array of soft elastic microwires is used both as anchors for tissue formation as well as sensors for recording tissue contraction. Conductive carbon electrodes are embedded into the plate to drive electrical stimulation for tissue maturation and pace tissue contraction during drug testing. The bulk of the device is made of rigid polystyrene plastic to eliminate drug-absorbing polydimethylsiloxane (PDMS). The platform has higher throughput than the current state-of-the-art devices, at a significantly reduced cost of manufacturing and tissue production.

Our tissue culture platform (referred to here as a Biowire II plate) was made of tissue culture plastic (polystyrene) yielding a PDMS-free final product, which minimizes drug absorption. The platform is based on a footprint of a standard 96-well plate, giving compatibility with widely used plate readers. The device was assembled from four components: 1) plate cap, 2) bottomless 96-well plate, 3) polymer wire array, and 4) patterned polystyrene base (FIGS. 2A-2C). The plate cap and bottomless 96-well plate are commercially available components. The polystyrene plate base was customized to match the 96-well plate format, with one microwell (L×W×H:5×1×0.2 mm) that aligns with the center of each bottomless well (FIG. 2A). Human pluripotent stem cell derived cardiomyocytes (hCMs) and human cardiac fibroblasts (10:1 ratio) in a hydrogel matrix (3.0 mg mL$^{-1}$ collagen and 15% (v/v) Matrigel) were cast in the microwells. To provide anchor points for tissue remodeling and compaction, two elastic microwires (diameter: 0.1 mm) positioned in parallel were cast across the microwell (FIG. 2B). Over time, hCMs/fibroblasts/hydrogel mixture seeded in the microwells self-organized into a 3D tissue suspended and anchored across the two parallel wires (FIG. 2C). Within one week, the tissues began to contract, bending the elastic polymer wires. Using calibration curves generated by a standard force sensor (MicroSquishier, CellScale) we were able to correlate the displacement of the polymer wires with the tissue contractile force.

Figure 8A:
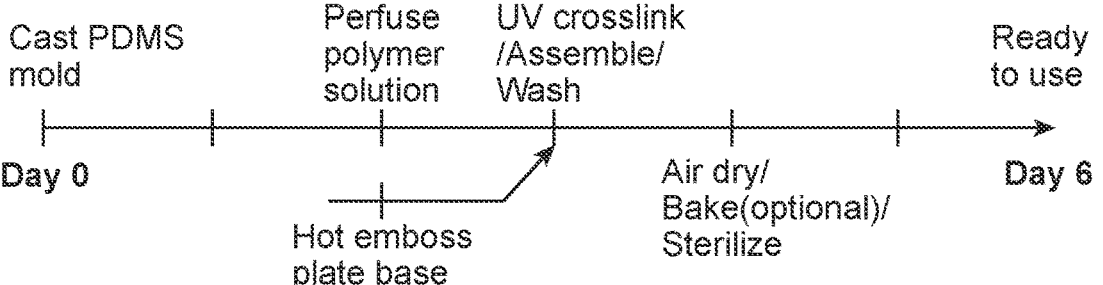
FIGS. 8A-8C show Biowire 96-well plate fabrication overview and dimensions.
Figure 8B:
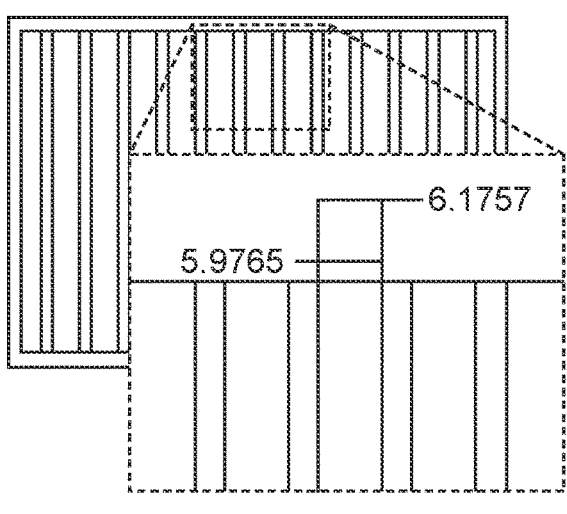

Although the entire device fabrication process can take up to six days, most steps that involve manual operation are short and multiple plates can be produced in parallel (FIG. 8A). The fabrication of the polymer wires and the base plate are concurrent. For these components, an SU-8 master mold was designed and fabricated using standard soft-lithography techniques according to the specifications shown in FIG. 8B and FIG. 8C. PDMS was then cast onto the SU-8 master to create a PDMS mold by crosslinking the PDMS at room temperature for 48 h. PDMS molds were then used to produce polymer wires, as well as to enable hot embossing of the polystyrene base plate. We chose to crosslink PDMS mold at room temperature rather than under heat to minimize the effect of thermal expansion. Thus, the resultant PDMS mold will retain the designed dimensions across a large surface area, such as the footprint of a 96-well plate. However, thermal expansion was still encountered during hot embossing of the base plate. Initially, we found that it was challenging to maintain the pre-defined plate dimensions without any shrinkage across this large footprint. Even a shrinkage of 0.1 mm across a length of 100 mm can result in significant misalignment between the wire and the microwells. Therefore, we empirically determined the degree of shrinkage after hot embossing, and readjusted the dimension of wire array to match the final dimensions of the plate base (FIG. 8B).

PDMS-Based Master Mold for Hot Embossing.

To make the polystyrene base plate, the back of the base plate PDMS mold was bonded to a 6 inch silicon wafer with plasma bonding or corona etching methods. Following bonding to the silicon wafer, the mechanical properties of the PDMS master were further strengthened by exposing to 150° C. for 30 min. A polystyrene sheet was molded against the PDMS master in a hot embosser, which yielded a customized polystyrene plate base. The fabrication of the PDMS master for hot embossing is significantly cheaper than the conventional metal etching approach to create a master. Although PDMS is softer than metal, which might lead to feature distortion during the hot-embossing process, we found that this issue can be circumvented by using low compression force with high temperature during embossing. One important benefit of a PDMS over a metal-based master is its ability for temporary distortion, to allow the easy release of embossed polystyrene sheet from the master. This is a major challenge when a hard material (polystyrene) is embossed against another hard material (metal master) where microfeatures must strictly possess vertical walls to prevent interlocking of two hard materials.

Figure 3A:
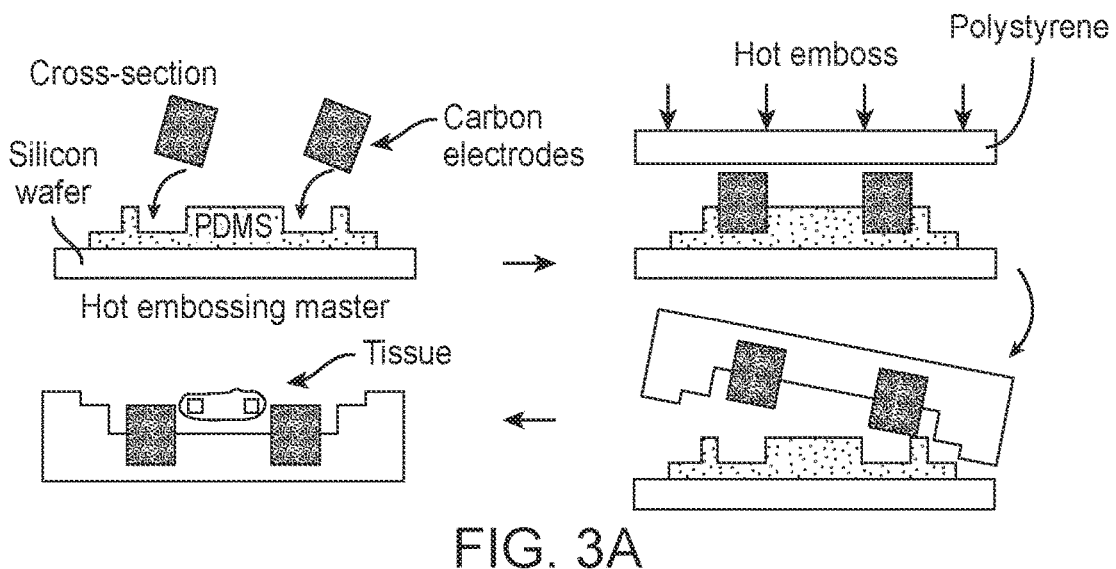
FIGS. 3A-3C show a Biowire plate base hot embossing, assembly, and post-treatment.
Figure 3B:
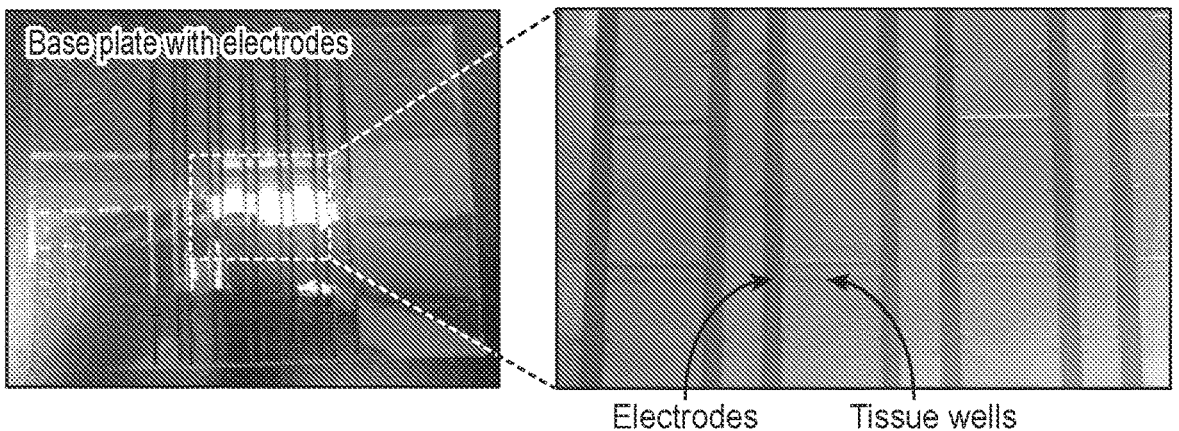
Figure 3C:
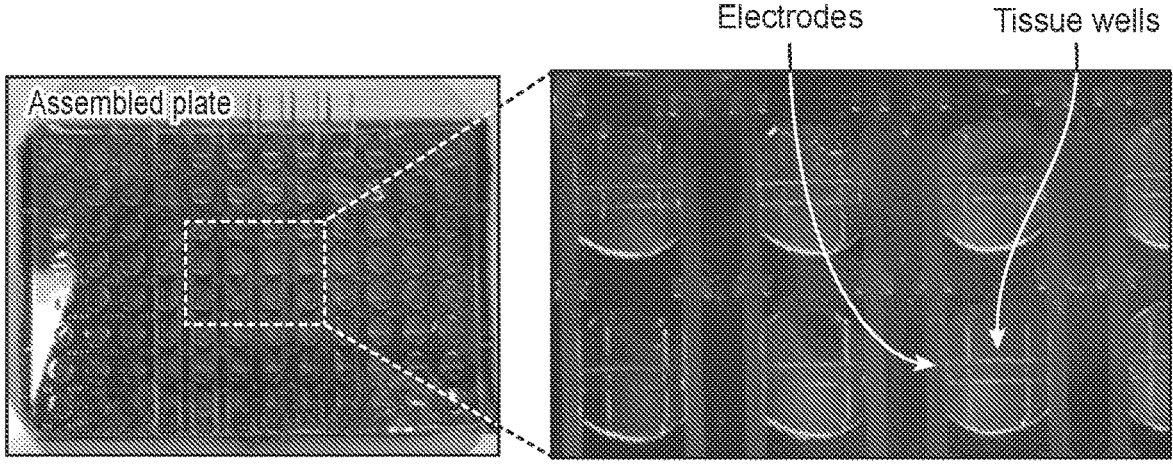
Figure 8C:
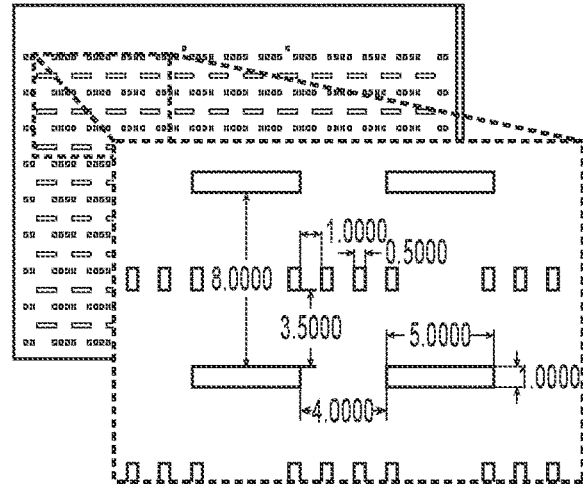
Figure 9A:
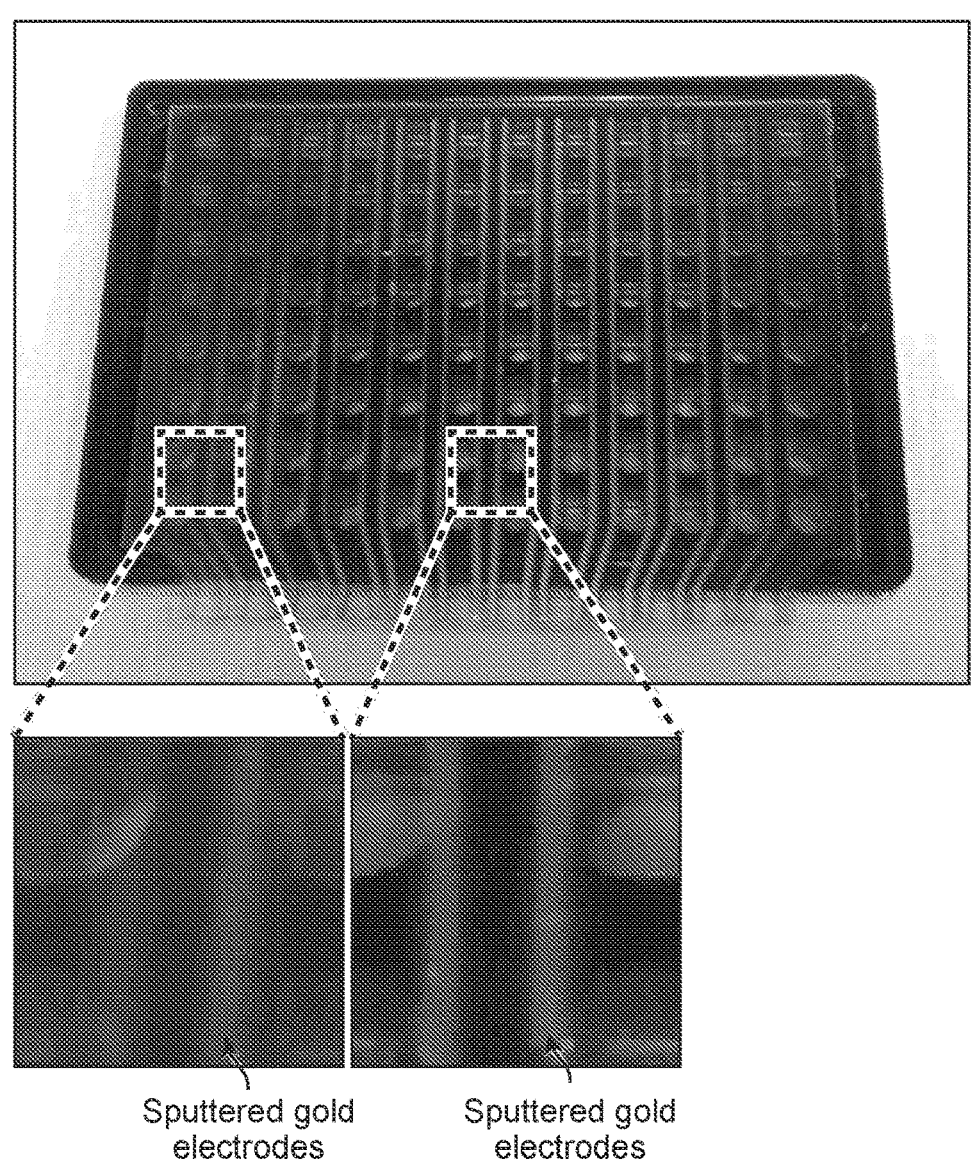
FIGS. 9A-9B show the Biowire 96-well plate with sputtered gold electrodes.
Figure 9B:
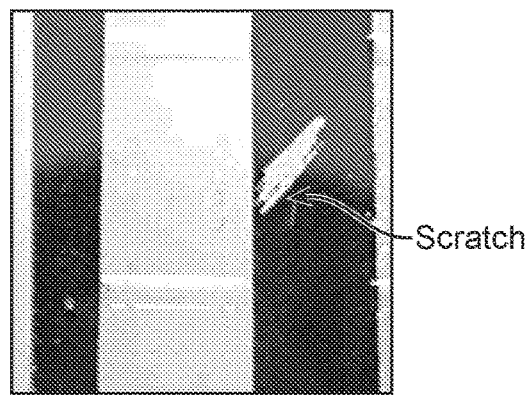
Figures 10A, 10B:
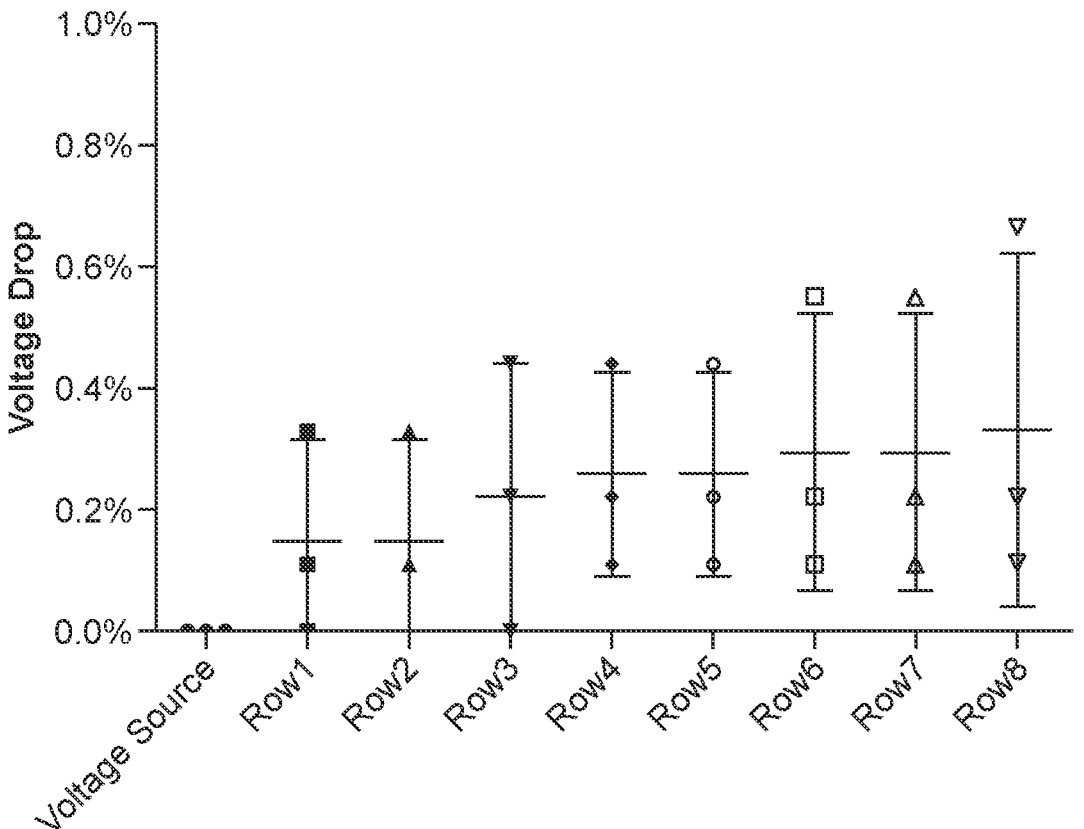
FIGS. 10A-10B show the voltage drops between carbon electrodes.

The plate incorporates a pair of built-in carbon electrodes around every microwell to generate a local electrical field across each tissue. Pacing the cardiac tissue with external electrodes has been shown to both mature the tissue over time and standardize beating frequency to ensure consistency in drug testing. For each column of wells, two long carbon electrodes were placed along the vertical well borders. FIG. 8C shows the design of the base plate. The rectangular posts around the microwells were designed to hold the carbon electrodes to the PDMS master mold prior to hot embossing (FIG. 3A). The carbon electrodes were embedded into the polystyrene sheet during hot embossing and were exposed on the plate surface and the side walls that make up the microwells (FIG. 3B, FIG. 3C). These exposed surfaces were strategically positioned to be as close to the tissue as possible and were sufficient to generate an electrical field along the tissue length. With embedding of electrodes with a thickness of 400 μm into the polystyrene base, electrical current was able to pass through with minimal resistance. This is beneficial in contrast with other methods, including our initial trials with sputtering (e.g., sputtered gold electrodes) that resulted in a thin conductive surface with a thickness on the nanometer scale (FIG. 9A). We found such conductive surfaces are difficult to coat uniformly across a large surface area, were easily damaged by scratching, resulted in high electrical resistance, and lacked long-term stability due to delamination (FIG. 9B). The percentage of voltage drop across the embedded carbon electrodes, compared to the voltage applied from the source, was negligible and consistent across the well-plate. (FIG. 10A).

Rapid Wire Casting on Microwells.

Figures 4A, 4B:
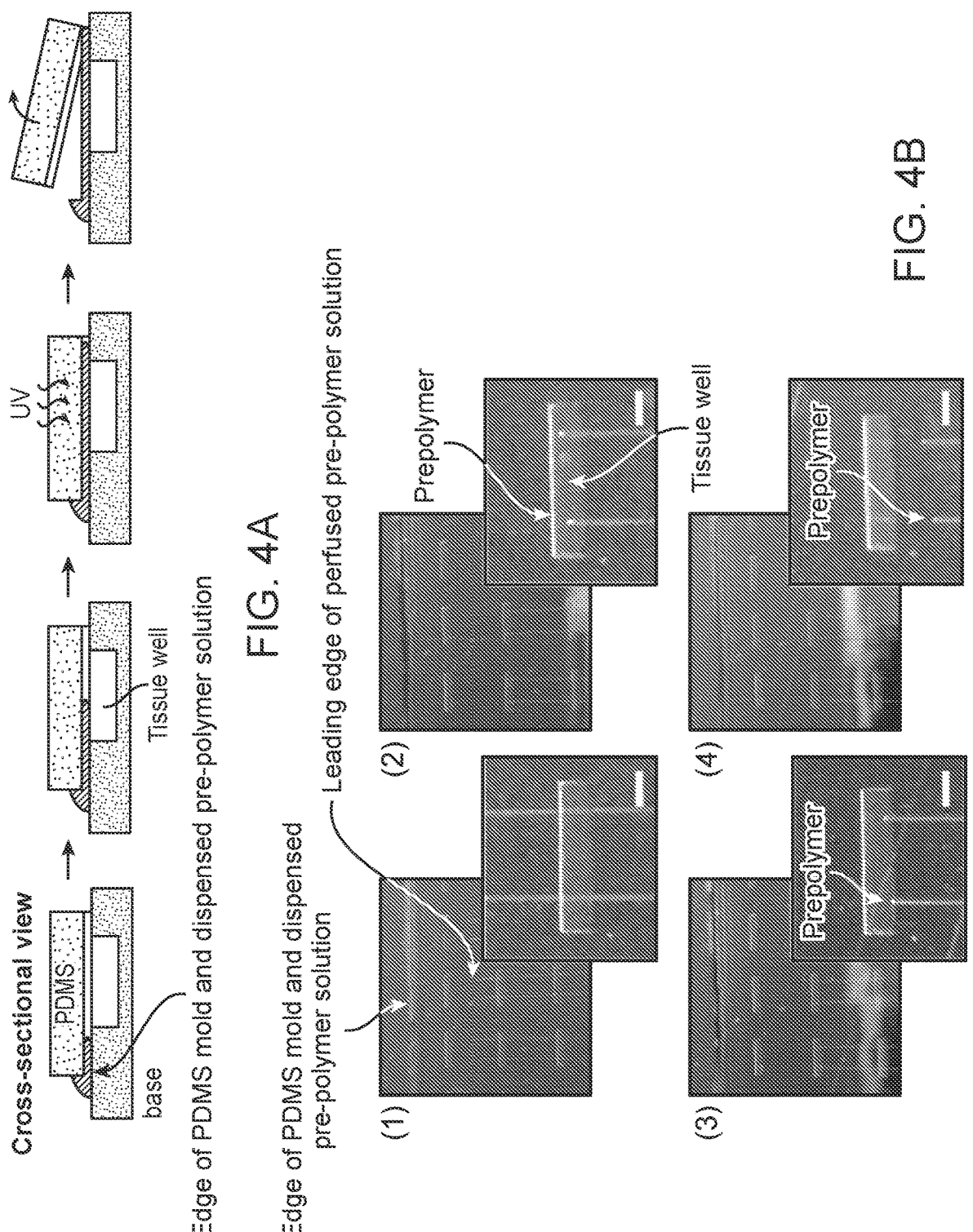
FIGS. 4A-4D show Rapid casting of suspended polymer wires in a 96-well plate format.
Figure 4C:
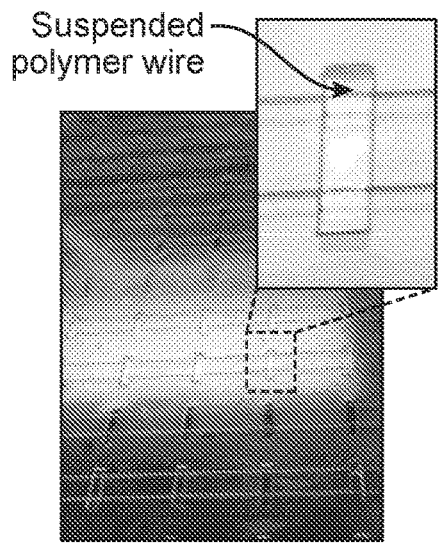
Figure 4D:
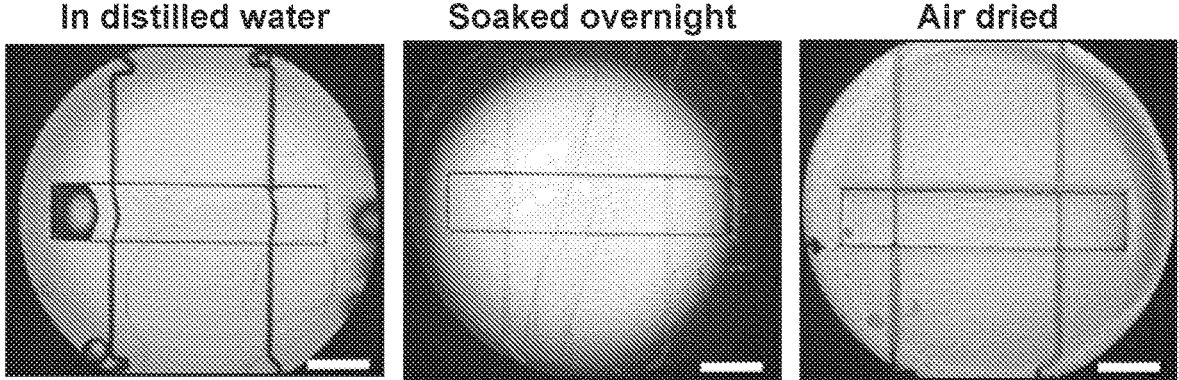

The casting of soft elastic polymer microwires suspended across an array of microstructures in a scalable manner can be challenging. To avoid this, we developed a method of molding and crosslinking the polymer wires directly over the microwell structure on the polystyrene base. To do this, the PDMS mold of the wire array was caped on top of the base plate with the microchannels on the mold facing the plate (FIG. 4A). Poly(octamethylene maleate (anhydride) citrate) (POMaC) prepolymer, a citric acid based polyester that can be crosslinked with UV light or heat energy, was deposited at the channel inlet. The prepolymer solution was drawn into the microchannels via capillary action. Notably, the prepolymer solution continuously filled the channels over the microwells, even though the cross-section of microchannels were not fully closed (FIG. 4B). Following full perfusion, the POMaC prepolymer was exposed to UV light to generate an array of crosslinked elastomeric wires, after which the PDMS mold was removed. To mitigate the effects of batch-to-batch variation of the bulk polymer solution to the mechanical stiffness of the UV-crosslinked polymer wires, the UV crosslinking energy was adjusted for each batch of polymers so that the Young's modulus (measured with a myograph as we described) of the bulk polymer after crosslinking is 33±3 kPa. UV-crosslinked POMaC wires consistently attached to the polystyrene base, resulting in multiple microwires cast across the entire plate, suspended across 96 microwells (FIG. 4C). This method enabled installation of 24 wires suspended across 96 microwells in a single step. The plate base cast with microwires was then fully assembled with a heat bonding step in the hot embosser to fuse a bottomless 96-well plate onto the polystyrene plate base casted with polymer microwires. Then, the assembled plate went through several postprocessing steps including washing in distilled water overnight, air drying, packaging, and gamma-ray sterilization. The elasticity of the microwire can be further fine-tuned with additional heat crosslinking by baking the entire plate at 70° C. for several days. The plates were stored at 4° C. and protected from light prior to use to minimize unnecessary heat and light exposures prior to use.

Plate Characterization and Use.

Figure 5A:
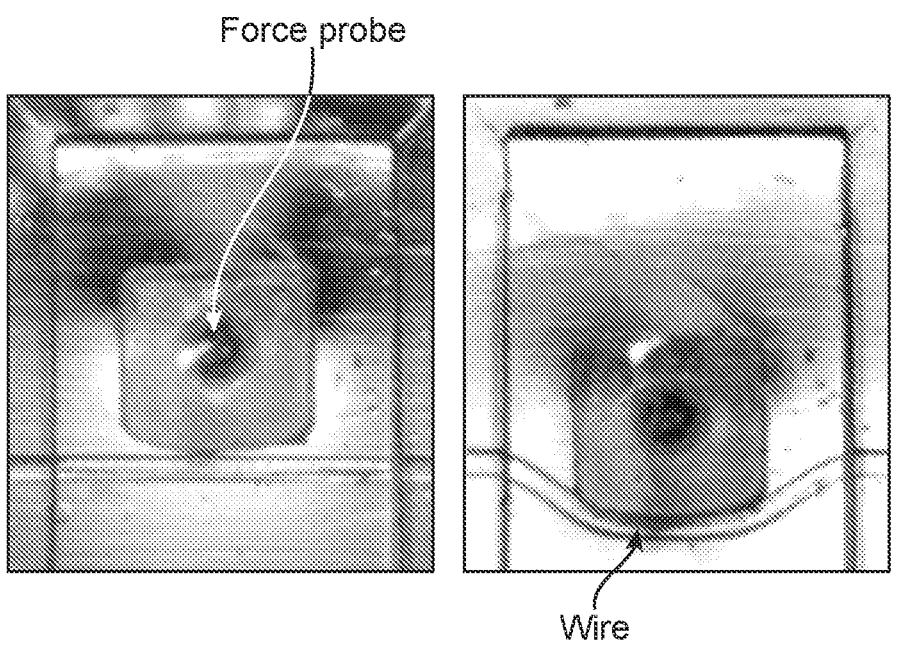
FIGS. 5A-5D show the characterization of polymer wires in the 96-well plate device.
Figure 5B:
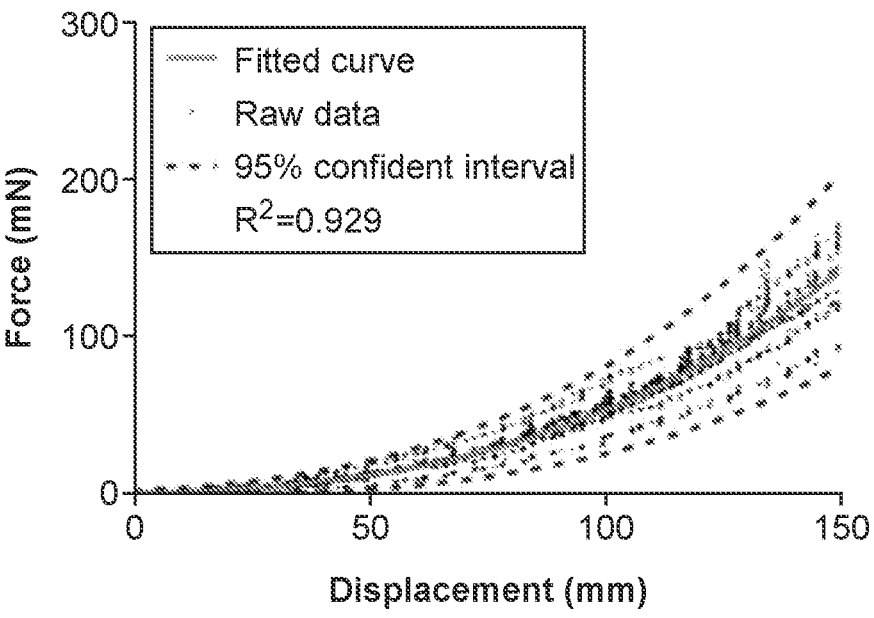
Figure 5C:
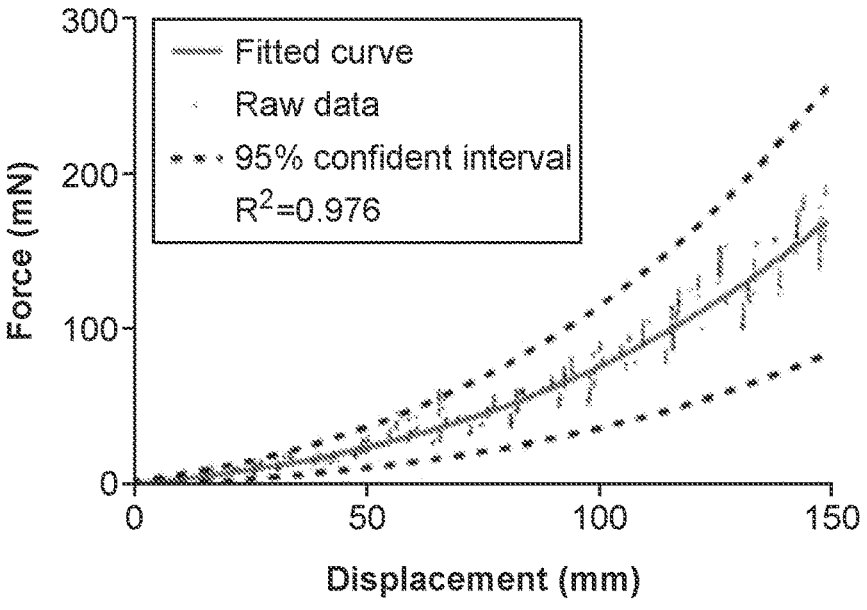
Figure 5D:
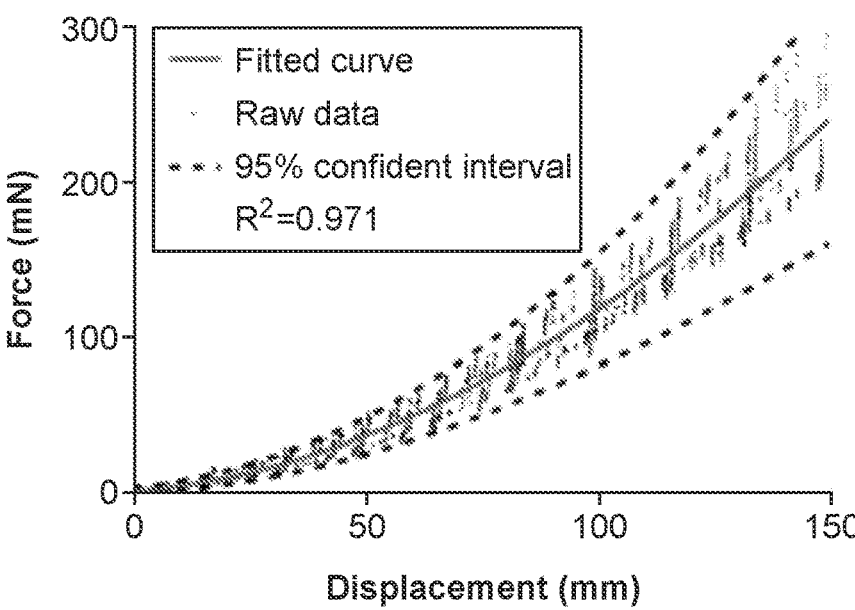
Figures 6A, 6B:
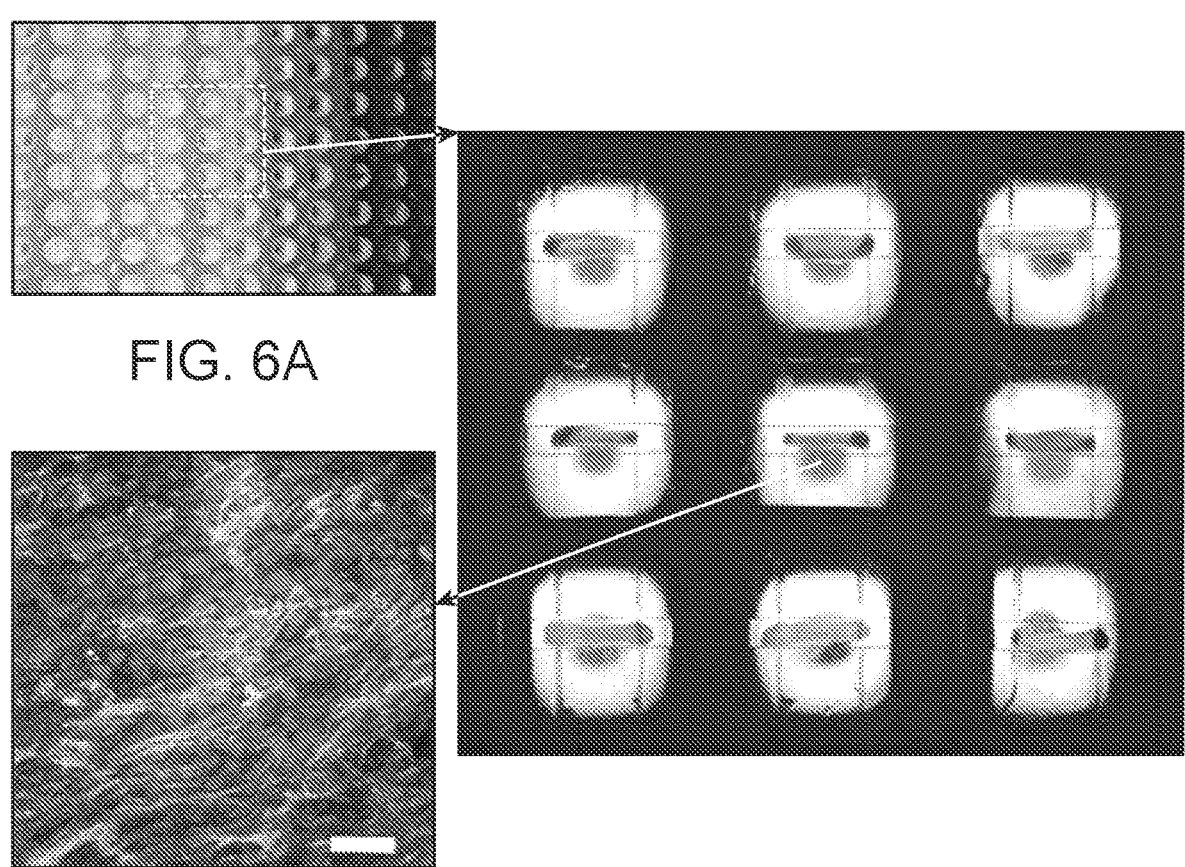
FIGS. 6A-6C show characterization of cardiac tissue cultured in the 96-well plate device.
Figure 6C:
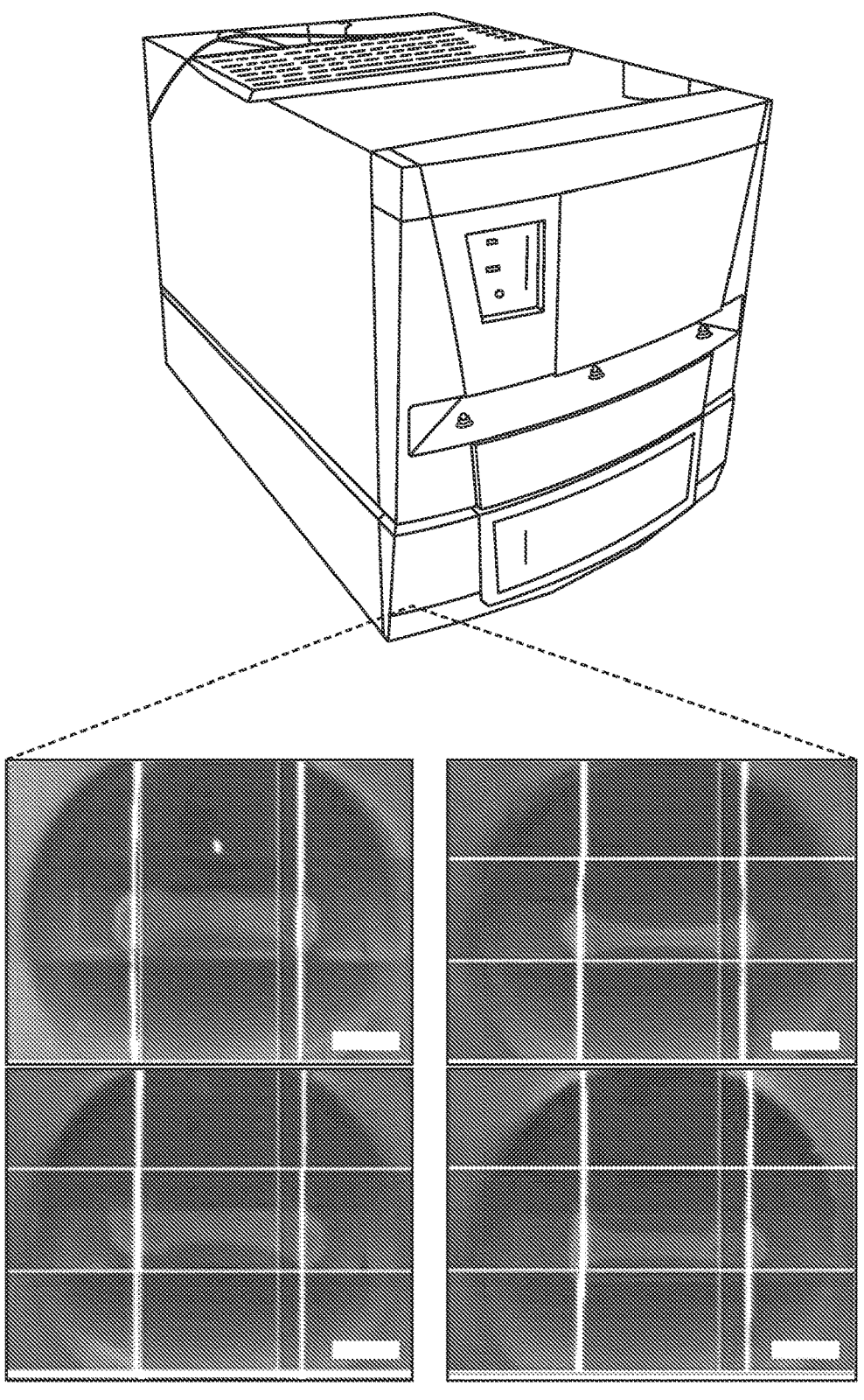
Figure 11A:
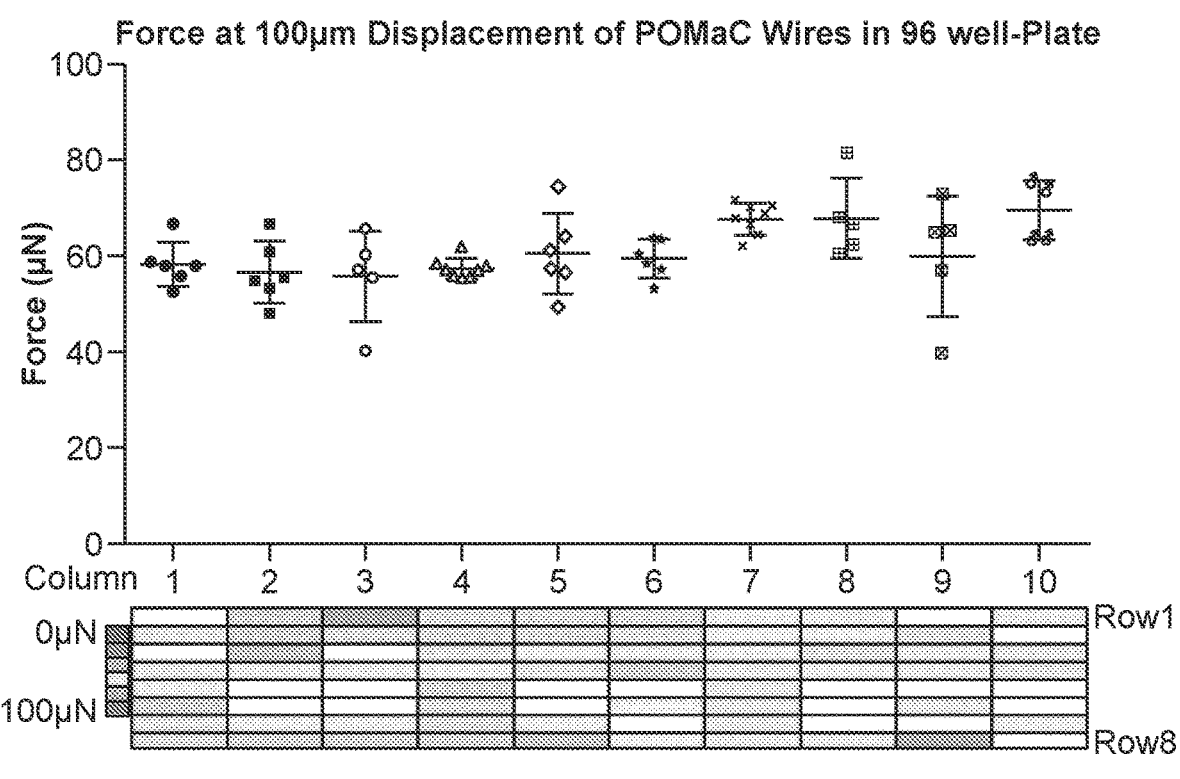
FIGS. 11A-11C show the consistency of POMaC wire properties across a 96-well plate.
Figure 11B:
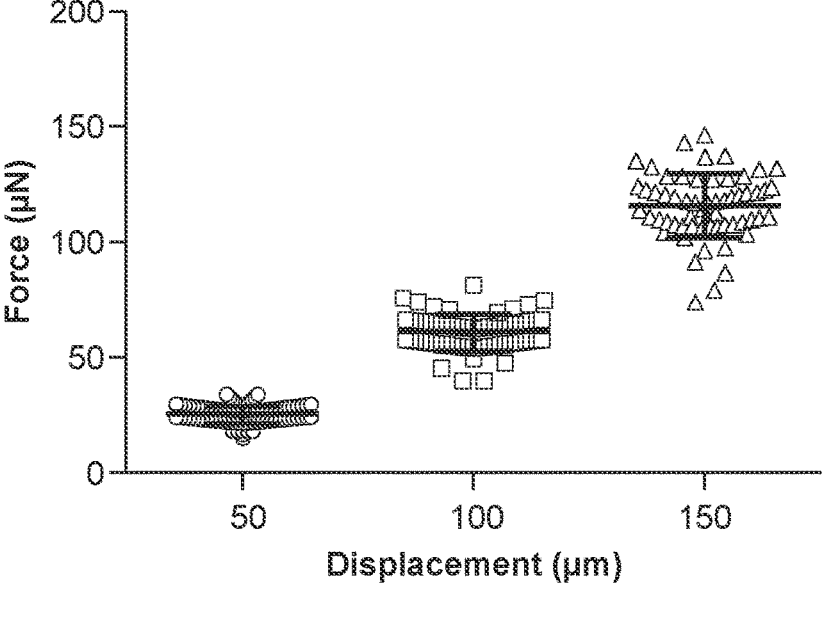
Figure 11C:
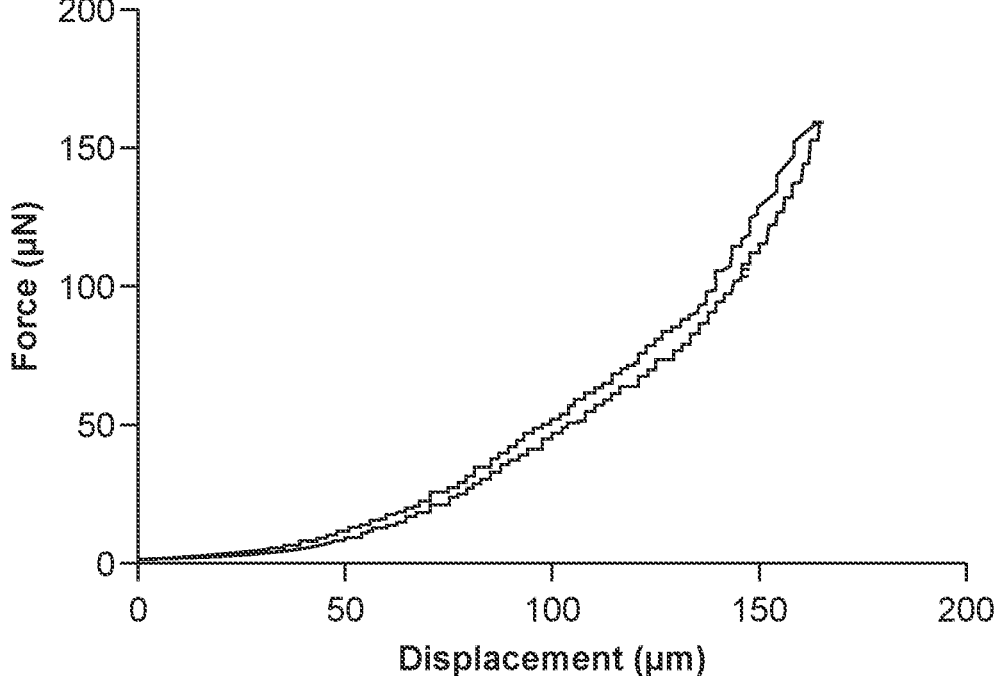

The cast polymer wires in the plate were used as both anchor points for tissues and force sensors to monitor change in contraction. To do so, the correlation between wire displacement and force generation was characterized. We used a commercially available microscale mechanical testing system, MicroSquisher (CellScale), to develop a force-displacement calibration curve (FIGS. 5A-5D). The probe tip was customized with a curvature similar to the tissue attachment to polymer wires. With the probe tip moving against the polymer wire at its center point, both force and displacement were recorded by MicroSquisher to develop force-displacement curves (FIG. 5A). The mechanical properties of the polymer wires can be further fine-tuned in post-processing by heat crosslinking. After two, four, and six days of heat crosslinking, the force-displacement curves and fitted polynomial equations are shown in FIGS. 5B-5D. The mechanical consistency of POMaC wires were demonstrated across the 96-well plate. There were no significant differences when the forces at 100 μm wire displacement were compared among the wells from different columns (FIG. 11C). The forces required to displace the wire for 50, 100, and 150 μm were also reproducible among all the wells (FIG. 11B). Furthermore, the tensile and relaxation curves of a representative polymer wire showed a minimal hysteresis (FIG. 11C). Microtissues cultured in each 96-well plate were able to grab the wires (FIG. 6A). The cardiac tissues also displayed well-aligned sarcomere structures when stained for sarcomeric α-actinin (green) and F-actin (red) (FIG. 6B). Since 96-well plates are a widely adopted tissue culture format, we demonstrated that the Biowire plate is also compatible with commercially available instruments, such as SpectraMax image cytometer for automatic imaging and analysis (FIG. 6C).

Long-Term Tissue Culture and Drug Testing with Electrical Stimulation.

Figure 7A:
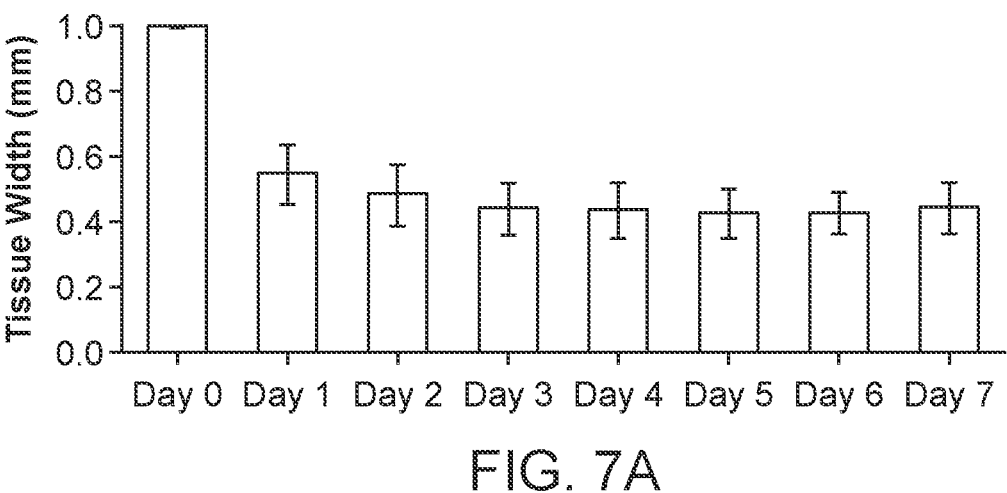
FIGS. 7A-7H show the functional assessment of human engineered cardiac tissues and their responses to thapsigargin after 12 days of electrical stimulation with built-in carbon electrodes.
Figure 7B:
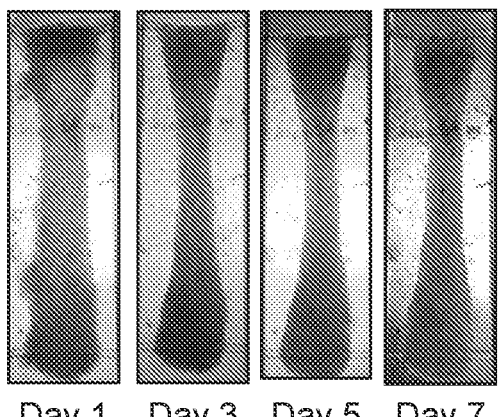
Figure 7C:
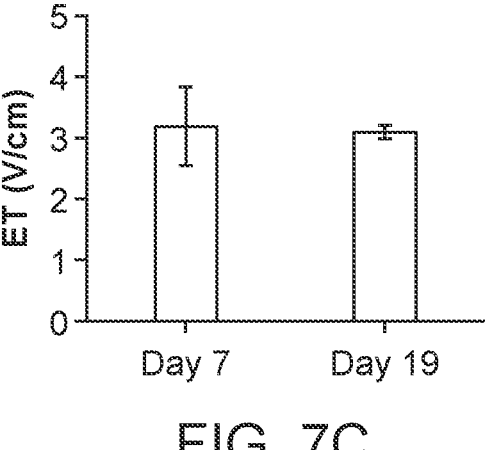
Figure 7D:
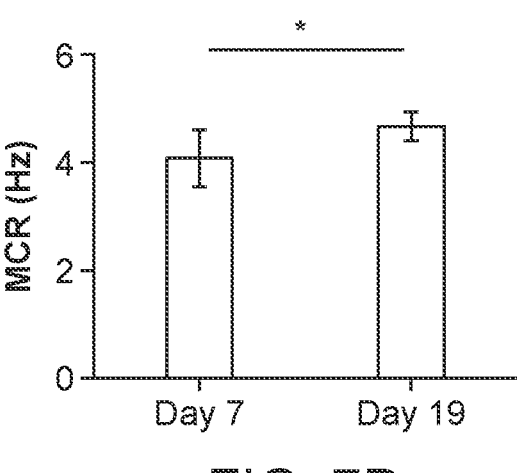
Figure 7E:
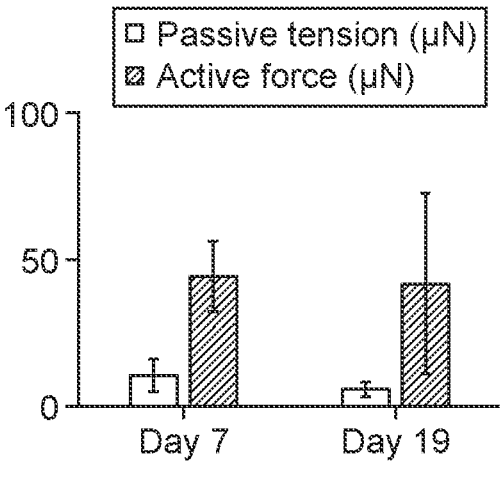
Figure 7F:
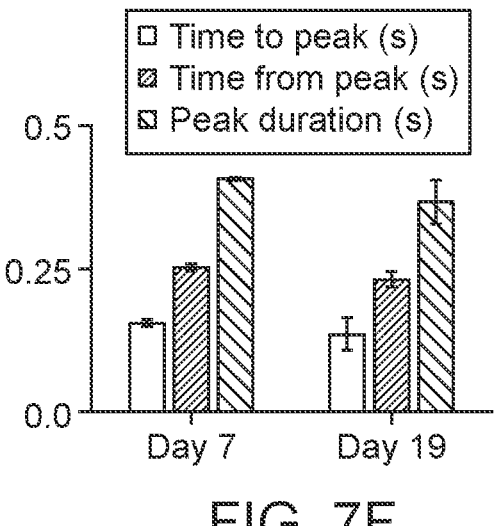
Figure 7G:
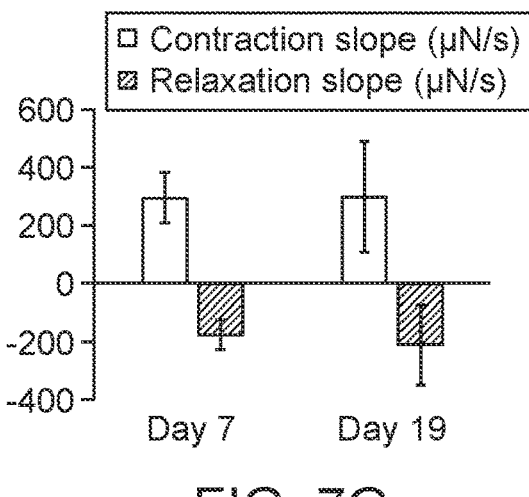
Figure 7H:
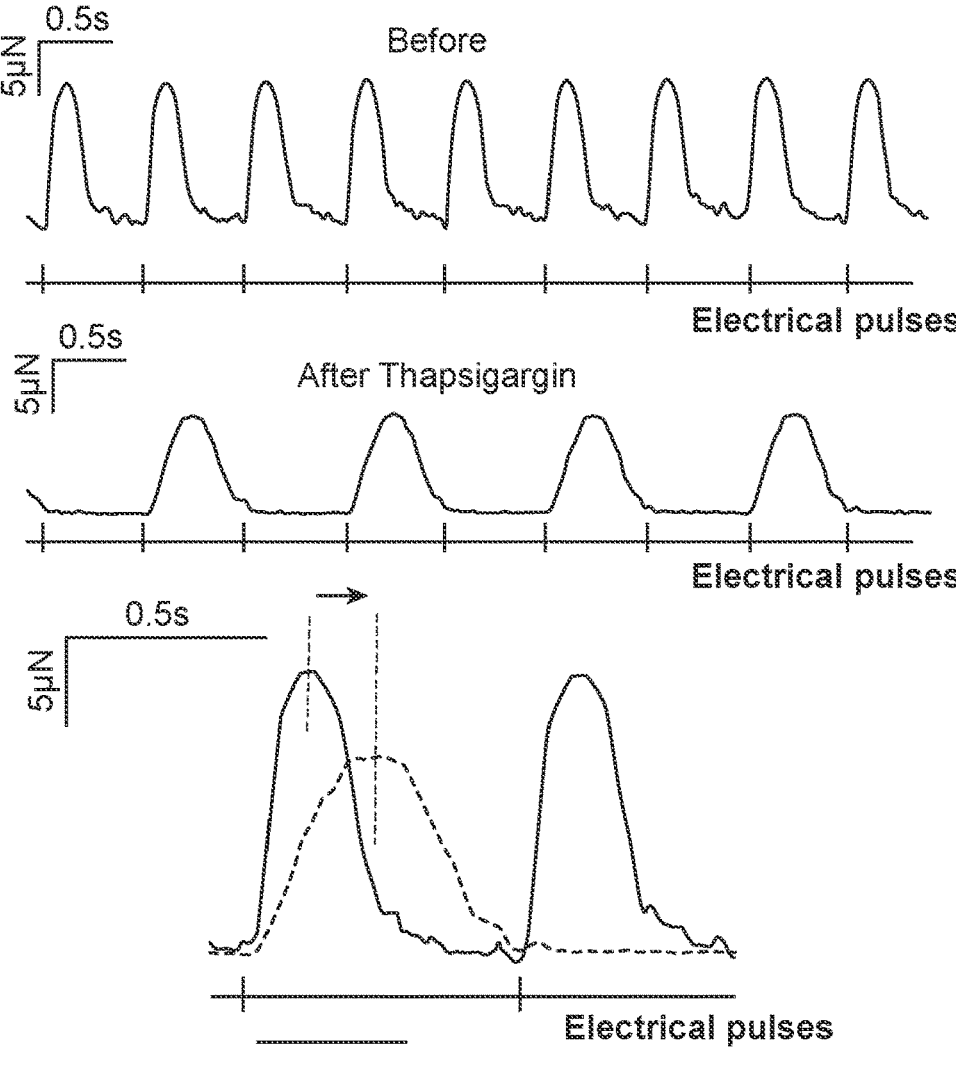

To characterize the utility of the platform for in situ measurements (e.g., force-displacement) and to conduct proof-of-principle studies to demonstrate that the platform can sup-port long-term cultures of cardiac tissues in a way similar to Biowire I, we then tracked the functional responses of the cardiac tissues cultured on the platform under electrical stimulation and treatments with clinically relevant drugs. To generate cardiac tissues, human iPSC derived cardiomyocytes co-cultured with human cardiac fibroblasts were seeded with hydrogel in the 96-well plate device. Tissue compaction in the first seven days was observed (FIG. 7A, FIG. 7B), with dramatic change in the first two days followed by stabilization after day 3. Electrical field stimulation of cardiac tissues was initiated at day 7 and continued for the additional 12 days. During this period, the electrical functionality of the tissues was improved as observed through a significantly increased maximum capture rate (FIG. 7C, FIG. 7D). The plate facilitated nondestructive evaluations of tissue contractile dynamics, which showed that passive tension, active force, time for contraction, and relaxation remained stable after 12 days of electrical stimulation (FIGS. 7E-7G). Thapsigargin ($50 \times 10^{-6}$ m), an inhibitor of sarcoplasmic reticulum function in cardiomyocytes, was added in the presence of electrical pacing (1.5 Hz), resulting in a prolonged tissue contraction and relaxation time (FIG. 7H). Furthermore, the frequency of tissue beating was decreased by half upon drug application despite the constant stimulation frequency (FIG. 7H).

Discussion

In this study, we developed a new method to rapidly cast suspended elastic microstructures (e.g., wires) onto an array of microfabricated topographical features (e.g., microwells). Thermal bonding with a hot embosser allowed us to fuse multiple parts of the plate together and to embed both carbon electrodes and polymer wires into the platform to create a controlled micro-environment around the tissue. Tissue function and response can be manipulated with electrical stimulation and tracked with built-in force sensors. In this multiwell plate format, each tissue was independently cultured and analyzed. Although the entire manufacturing process requires six days from production to storage, the entire process is scalable as the production workload will not increase with increasing number of wells in the plate. This means the same process could be adapted to make 6-well, 24-well, 96-well, or even 386-well plates. Furthermore, multiple plates can be fabricated in parallel to achieve higher production throughputs, compatible with industrial manufacturing process. Up to 96 tissues can be cultured on a single plate; an experimentation throughput is significantly higher than in many conventional organ-on-a-chip platforms. Furthermore, the formation of a cardiac tissue takes as few as 100,000 cells. Currently, cell seeding is still a limiting step for high-throughput tissue production. However, enabled by the open well design, automatic cell dispensers that are widely available in the pharmaceutical industry, could be used to scale up the cell-seeding and operation of this multiwell plate platform.

Material post-processing after plate assembly also allowed adjustment to the deflection-force profiling in this system. By characterizing the mechanical properties of the elastic micro-wires, the functional readouts of tissue contractile dynamics can be deduced. The mechanical properties of the POMaC wire were reproducible among all the wells in the 96-well plate, which indicates the reliability of this casting method. Since the polymer wires are always positioned at the identical height, the tissue height is always constant enabling easy monitoring, in contrast to post-based platforms, where tissue vertical position is non-uniform. Nondestructive functional readouts are crucial for long term chronic drug studies. For our application, we demonstrated rapid casting of soft elastic microwires for the purpose of cardiac tissue culture. However, more complex suspended microstructures could be cast to enable the formation of more complex tissue structures with the same method. This platform also incorporates built-in electrodes that can stimulate tissues continuously for at least 12 days to assist in tissue maturation. The highly conductive carbon electrodes minimized the voltage drop from the voltage source to the electrodes, therefore facilitating a precise control of culture and testing environment. The presence of electrodes plays a crucial role in probing drug responses. For instance, when testing drugs in acute or chronic formats, chronotropic effects from the drugs can be isolated from inotropic effects by stimulating the tissue at a physiologically relevant frequency. With thapsigargin treatment, we showed slowed tissue contraction and relaxation, and a reduced frequency despite of the fixed pacing frequency. This implied the relaxation of the tissue was too slow to start the next depolarization until the relaxation of the previous contractile cycle is finished, thus, the frequency is reduced by half. Therefore, our platform was able to recapitulate the known in vivo effects of this compound, suggesting its applicability as a relevant in vitro screening platform.

Herein, we described a facile approach to manufacture an array of elastic microwires for scalable 3D cardiac tissue culture and contractile force readout in a 96-well plate format. This arrayed tissue culture plate can facilitate microscale tissue cultivation with a minimal number of cells, promote cardiomyocyte maturation with built-in carbon electrodes, as well as provide non-invasive functional assessments for cardiotoxicity prediction. Based on the ease and high throughput of fabrication, and the availability of high-fidelity cardiac tissue, the featured platform provides a valuable tool for assessing tissue responses of pharmacological compounds.

Experimental Procedure.

POMaC Prepolymer Solution Preparation: POMaC was used to prepare the built-in polymer sensors. POMaC was synthesized by first preparing a prepolymer gel through a polycondensation reaction. Citric acid (Caledon, A00019), maleic anhydride (Sigma, 63200), and 1,8-octanediol (Sigma, 03303) were combined in a triple necked 250 mL round bottom flask with an equimolar amount of carboxylic acid (citric acid+maleic anhydride) to alcohol (1,8-octanediol) functional groups and a 1:4 ratio of citric acid to maleic anhydride. The reaction solution was heated to generate a melt polymerization solution and carried out at 150° C. with stirring at 200 rpm for 5 h under nitrogen flow. The resultant gel was dissolved in 1,4-dioxane (Sigma, D201863) followed by a dropwise precipitation in deionized water to remove unreacted monomers or short chain oligomers. The aqueous phase was then decanted and undissolved prepolymer was collected and concentrated. Purified prepolymer was mixed with poly(ethylene glycol) dimethyl ether (PEGDM Mw≈500) (Sigma, 445886) at 6:4 (w:w) ratio and 5 (w/w) % photo-initiator, 2-hydroxy-1-[4(hydroxyethoxy) phenyl]-2-methyl-1-propane (Sigma, 410896). The resulting solution was stored at 4° C. until use in sensor casting.

Fabrication of Base Plate with Built-In Carbon Electrodes.

A repeated pattern consisting of rectangular microwells (5×1 mm, L×W) and rectangle notches (1×0.5 mm, L×W) was designed with AutoCAD. Spacing from adjacent microwells (in all directions) was 9 mm to achieve compatibility with conventional 96-well tissue culture plates. Using soft lithography, an SU-8 photoresist master mold was generated using a photomask derived from the computer model and used to produce a negative PDMS (Sylgard 184 silicone elastomer kit, Dow Corning, 01064291) master mold with a feature height of 200 μm. Briefly, silicone elastomer base and the curing agents were vigorously mixed in the cup at 5:1 (w:w) ratio and the mixture was poured onto the SU-8 master mold to cure at room temperature. The PDMS master mold was then fixed to a silicon wafer by plasma bonding or corona etching. To embed the electrodes into the polystyrene base plate, carbon electrodes were first placed on the PDMS mold and fixed between the rectangle notches. Carbon electrodes were custom computer numerical controlled (CNC) machined at Ohio Carbon Blank. The electrodes were isostatically pressed carbon/graphite (Cat No. AR-14, Ohio Carbon Blank). Then a blank polystyrene sheet and a silicon wafer were placed on top and loaded into an EVG 520 Hot Embosser. The temperature and pressing force were gradually increased to 190° C. and 3000 N, with an internal pressure of $5\times10^{-3}$ mbar. After temperature and pressure returned to ambient conditions, the resultant patterned polystyrene base embedded with carbon electrodes was released from the PDMS mold. The edges were trimmed and ready for use.

Fabrication of PDMS Mold and Wire Installation in Batch

To fabricate the POMaC wires, a PDMS mold with 24 microchannels (cross-section: 100×100 μm) positioned in parallel was fabricated from a SU-8 master mold, as previously described. Silicone elastomer base and curing agent were vigorously mixed in the cup at 15:1 ratio and the 15 g of the mixture was poured onto the SU-8 master mold to cure at a room temperature. With edge trimming to vertically open the channel ends, the channel side of PDMS mold was cleaned with clear tape to remove dust particulate. The PDMS mold was then gently pressed on top of the embossed polystyrene sheet with adjustment of channel position and orientation and position to align the polymer wire location with the microwells. POMaC pre-polymer solution was dispensed to the top edge of the PDMS mold with a syringe, and the pre-polymer was perfused by capillary action in the dark for 48 h at room temperature. Following perfusion, the polymer was cross-linked under UV light (1500 mJ cm$^{-2}$) to generate an elastomeric material network. The excess nonperfused POMaC polymer was removed and the PDMS mold was slowly peeled away from the plate base, leaving behind the polymer wires which remain adhered to the polystyrene sheet.

Thermal Bonding of Base to a Bottomless 96-Well Plate

A bottomless 96-well plate was placed, base up, on a flat surface and a base plate equipped with wires and electrodes was placed against it, aligned to center the polymer wire pairs in individual wells. A drop of acetone was applied at the corners of the plate between the base and the plate to temporarily bond the plastic layers, then the combination was fully bonded by hot embossing. The base face was gradually heated to 184° C. with a pressing force of 700 N, and an internal pressure of $5\times10^{-3}$ mbar with maintenance of the top heating surface at 96° C.

Post-Assembly Processing

Following the embossing process, wells of bonded plates were filled with distilled water and incubated overnight (37° C., 5% CO$_2$). Water was then removed and the plate was air dried under sterile conditions. The plate was then baked (70° C.) for six days and subjected to gamma ray sterilization. After sterilization, the plate was stored at 4° C. shielded from light.

Plate Characterization.

To measure the bulk polymer Young's modulus, a myograph machine (Kent Scientific), composed of a mechanical stretcher and a force transducer, was used to stretch strips of POMaC polymers (0.3×1×10 mm) crosslinked with UV light (1500 mJ cm') in PBS solution. The slope of the resulting stress-strain curve was used to calculate the Young's modulus. Polymer wire force/displacement curves in the wells were characterized using a commercially available micromechanical tester, MicroSquisher (Cell Scale). Testing probes (diameter=0.1524 mm) were modified with customized tips (half ellipse, 4:1 diameter ratio with long diameter of 0.5, 0.7, and 0.8 mm) fabricated from an SU-8 master by soft lithography and attached to the provided tungsten probe using an adhesive (T-GSG-01 Titan Gel). Polymer wires were soaked in medium for seven days prior to testing. Testing tips were centered in the microwell, then polymer wires were displaced at the center using the probe tips moving perpendicular to the long axis of the wire, with recording of the corresponding force output (n≥12). The experimental data for each custom tip were fit to a third-degree polynomial equation, generating a standard force curve for each custom probe. For consistency across the plate, measured forces at 100 mm displacement were compared among right wires in each well. The two outermost columns were omitted from the measurements on purpose, as it was found that the pressure at the edges created nonuniformities in the two outermost columns.

Voltage Drop Along the Electrode

After the plate assembly, carbon electrodes along a column were connected to a voltage source (9 V battery). A handheld multiscope (Extech, 381275) was used to measure the voltage differences across each pair of carbon electrodes in different wells (n=3 wells per row). Voltage drop was calculated using the differences in the voltage between the carbon electrodes and the voltage source divided by the voltage from the voltage source.

Hydrogel Preparation

Collagen hydrogel (500 µL) was prepared by combining high concentration rat tail collagen (153 µL at 9.82 mg mL$^{-1}$, Corning) with 15% (v/v) Matrigel (75 µL, BD Biosciences), NaHCO$_3$ (50 µL at 2.3 mM, Sigma), NaOH (5 µL at 10 mM, Sigma), deionized sterile H$_2$O (167 µL) and 1×M199 (50 µL, Sigma) to result in a final collagen concentration of 3.0 mg mL$^{-1}$.

Cardiomyocyte Preparation and Generation of Engineered Cardiac Tissues.

Predominantly ventricular cardiomyocytes (CMs) were derived from the hiPSC line BJ1D, using monolayer differentiation protocols as previously described. At day 21 of differentiation, cardiomyocytes were disassociated into single cells with previously established methods. Briefly, 1 mg mL$^{-1}$ of collagenase type II (Worthington, LS004205) in Hank's Balanced Salt Solution was added to the monolayer cardiomyocyte cultures and incubated overnight at room temperature. The disassociated cells were mixed with cardiac fibroblasts (Lonza, NHCF-V) in a 10:1 cell number ratio. The mixed cells were pelleted and remixed in collagen hydrogel at 5.5×10$^7$ cells mL$^{-1}$. The cell-gel mixture was seeded at 2 mL per microwell. A droplet of media was placed on the wall of the well to keep the moisture until gelation was complete. The plate was incubated at 37° C. and 5% CO$_2$ for 10 min followed by media addition. After seeding (day 0), the tissues were cultured for seven days to allow remodeling around the POMaC wires. Bright field images of the tissues were taken daily to monitor tissue morphology. By day 7, the tissues synchronously contracted and deflected the POMaC wire with each contraction.

Imaging Tissue Morphology in Batch

SpectraMax MiniMax 300 Imaging Cytometer was used to image tissues in the well plate to monitor the daily morphology changes of tissues. Nine pictures were taken in each well of the 96-well plate and automatically stitched together to show the entire view of the well. Contractile Analysis via 4',6-Diamidino-2-Phenylindole (DAPI) Channel Imaging Spontaneous and paced (1 Hz) contraction was imaged using bright field microscopy (4× objective). The blue channel (10× objective; $\lambda_{ex}$=350 nm, $\lambda_{em}$=470 nm; 100 frames s$^{-1}$, 5 ms exposure) was used to record and analyze tissue contractile behavior, and data was output using custom MATLAB code to track wire displacement. Average tissue width and width of the tissue (Tw), attachment site to the polymer sensor were measured using bright field images at the relaxed state. Passive displacement of polymer sensors was assessed in blue channel. Total deflection and passive deflection of polymer sensors (mm) were converted to force (mN) using calibration curves that were generated as described in the plate characterization section. The final readouts for the total and passive forces were interpolated according to the Tw and custom tip sizes. The active forces were the difference between total and passive force. The custom MATLAB code was used to calculate the passive force, active force, contraction, and relaxation duration.

Immunostaining and Confocal Microscopy

Tissues were fixed with 4% paraformaldehyde, permeabilized with 0.2% Tween20, and blocked with 10% fetal bovine serum. Immunostaining was performed using the following antibodies: mouse anti-α-actinin (Abcam; 1:200) and the donkey anti-mouse-Alexa Fluor 488 (Abcam; 1:400). Phalloidin-Alexa Fluor 660 (Invitrogen; 1:200) was used to stain F-actin fibers. Confocal microscopy images were obtained using an Olympus FluoView 1000 laser scanning confocal microscope (Olympus Corporation).

Tissue Maintenance and Drug Testing with Electrical Stimulation

Each well of 96-well plate contained 300 mL of culture medium, which was changed every 24 h. With built-in force sensor and electrodes, tissues were able to be assessed in situ in terms of their contractile dynamics and drug responses. Before testing, a bright field video of tissue was taken to obtain necessary measurements for force calculation. During testing, pacing voltage was increased to 110% of excitation threshold. One polymer wire (blue channel, 10× magnification) was imaged consistently for comparison. Once baseline video was taken, 0.3 µL of thapsigargin (50×10$^{-3}$ m in DMSO) was added into the well with gelloading pipette tip. After 15 min, video was taken again after thapsigargin was in effect. The videos were analyzed using the custom MATLAB software.

Statistical Analysis

Statistical analysis was performed using Sigma Plot 12.0 or Prism 6.0. Differences between experimental groups were analyzed by Student's t-test or one-way ANOVA. Normality test (Shapiro-Wilk) and pairwise multiple comparison procedures (Tukey or Holm-Sidak method) were used for one-way ANOVA. $p<0.05$ was considered significant for all statistical tests. All data were shown as mean±standard deviation. Sample size (n) for each statistical analysis was stated in the Figure captions.

REFERENCES

P. Liang, F. Lan, A. S. Lee, T. Gong, V. Sanchez-Freire, Y. Wang, S. Diecke, K. Sallam, J. W. Knowles, P. J. Wang, P. K. Nguyen, D. M. Bers, R. C. Robbins, J. C. Wu, *Circulation* 2013, 127, 1677.

Y. Zhao, A. Korolj, N. Feric, M. Radisic, *Expert Opin. Drug Saf.* 2016, 15, 1455.

S. Morgan, P. Grootendorst, J. Lexchin, C. Cunningham, D. Greyson, Health *Policy* 2011, 100, 4.

G. Gintant, P. T. Sager, N. Stockbridge, *Nat. Rev. Drug Discovery* 2016, 15, 457.

M. Tiburcy, J. E. Hudson, P. Balfanz, S. Schlick, T. Meyer, M. L. Chang Liao, E. Levent, F. Raad, S. Zeidler, E. Wingender, J. Riegler, M. Wang, J. D. Gold, I. Kehat, E. Wettwer, U. Ravens, P. Dierickx, L. W. van Laake, M. J. Goumans, S. Khadjeh, K. Toischer, G. Hasenfuss, L. A. Couture, A. Unger, W. A. Linke, T. Araki, B. Neel, G. Keller, L. Gepstein, J. C. Wu, W. H. Zimmermann, *Circulation* 2017, 135, 1832.

S. S. Nunes, J. W. Miklas, J. Liu, R. Aschar-Sobbi, Y. Xiao, B. Zhang, J. Jiang, S. Massé, M. Gagliardi, A. Hsieh, N. Thavandiran, M. A. Laflamme, K. Nanthakumar, G. J. Gross, P. H. Backx, G. Keller, M. Radisic, *Nat. Methods* 2013, 10, 781.

J. Shim, A. Grosberg, J. C. Nawroth, K. K. Parker, K. Bertoldi, *J. Bio-mech.* 2012, 45, 832.

J. U. Lind, T. A. Busbee, A. D. Valentine, F. S. Pasqualini, H. Yuan, M. Yadid, S. J. Park, A. Kotikian, A. P. Nesmith, P. H. Campbell, J. J. Vlassak, J. A. Lewis, K. K. Parker, *Nat. Mater.* 2017, 16, 303.

S. Schaaf, A. Shibamiya, M. Mewe, A. Eder, A. Stöhr, M. N. Hirt, T. Rau, W. H. Zimmermann, L. Conradi, T. Eschenhagen, A. Hansen, *PLoS One* 2011, 6, e26397.

T. Boudou, W. R. Legant, A. Mu, M. A. Borochin, N. Thavandiran, M. Radisic, P. W. Zandstra, J. A. Epstein, K. B. Margulies, C. S. Chen, *Tissue Eng., Part A* 2012, 18, 910.

M. W. Toepke, D. J. Beebe, *Lab Chip* 2006, 6, 1484.

E. Berthier, E. W. Young, D. Beebe, *Lab Chip* 2012, 12, 1224.

R. T. Tran, P. Thevenot, D. Gyawali, J. C. Chiao, L. Tang, J. Yang, *Soft Matter* 2010, 6, 2449.

B. Zhang, M. Montgomery, M. D. Chamberlain, S. Ogawa, A. Korolj, Pahnke, L. A. Wells, S. Massé, J. Kim, L. Reis, A. Momen, S. S. Nunes, A. R. Wheeler, K. Nanthakumar, G. Keller, M. V. Sefton, M. Radisic, *Nat. Mater.* 2016, 15, 669.

B. Zhang, B. F. L. Lai, R. Xie, L. Davenport Huyer, M. Montgomery, M. Radisic, *Nat. Protoc.* 2018, 13, 1793.

S. Suomalainen, V. Kytöniemi, M. Mehto, *Reproducible Dispensing of Live Cells with the Thermo Scientific Multidrop Combi Reagent Dis-penser*, Thermal Fisher Scientific, Vantaa, Finland 2009.

X. Lian, J. Zhang, S. M. Azarin, K. Zhu, L. B. Hazeltine, X. Bao, C. Hsiao, T. J. Kamp, S. P. Palecek, *Nat. Protoc.* 2013, 8, 162.

L. Yang, M. H. Soonpaa, E. D. Adler, T. K. Roepke, S. J. Kattman, M. Kennedy, E. Henckaerts, K. Bonham, G. W. Abbott, R. M. Linden, L. J. Field, G. M. Keller, *Nature* 2008, 453, 524.

What is claimed is:

1. A system comprising:
two or more devices, wherein each device comprises:
a substrate;
at least one pair of electrodes embedded at least partially in the substrate, the pair of electrodes having a first electrode and a second electrode separated by a gap;
at least one well having a bottom on the substrate, a first end in contact with the first electrode, and a second end in contact with the second electrode, the well configured for growing a tissue from cells seeded therein, wherein the pair of electrodes is configured to apply an electrical stimulation to the tissue; and
at least two elastic sensing elements disposed across the well such that there is a gap between the sensing elements and the bottom of the well, wherein the sensing elements are configured to: (a) permit attachment of the tissue formed therebetween, thereby suspending the tissue above the bottom of the well, and (b) deform in response to a contractile force exerted on the sensing elements by the tissue, thereby simulating a physiological environment that is native to the tissue and/or permitting measurement of the contractile force; and
a stimulator having two or more driver boards, wherein each driver board is configured to apply an electrical stimulation between each pair of electrodes of each device, thereby permitting the stimulator to independently control the application of the electrical stimulation between each pair of electrodes.

2. The system of claim 1, further comprising an interface tray having a hinged lid and configured to couple the devices electrically to the stimulator; or
an optical microscope configured to produce an image of the sensing elements and/or tissue in each device; or
a computing device coupled to the microscope and configured to analyze the image and/or control the stimulator.

3. The system of claim 1, wherein each device comprises two or more wells, 6 wells, 12 wells, 24 wells, 48 wells, or 96 wells; or wherein each device comprises 2 to 25 sensing elements per well.

4. The system of claim 1, wherein the pair of electrodes is fully embedded in the substrate or wherein the electrodes comprise conductive carbon, gold, platinum, palladium, stainless steel, tin, tungsten, titanium, or a combination thereof, optionally wherein the conductive carbon is non-porous.

5. The system of claim 1, wherein the first electrode and the second electrode are separated by a gap in the range of 1 mm to 5 cm; or wherein the first electrode is parallel or substantially parallel to the second electrode.

6. The system of claim 1, wherein each device comprises two or more pairs of electrodes, at least one well positioned in between each pair of electrodes, optionally wherein each of the electrodes is parallel or substantially parallel to each other, or two or more wells are positioned between each pair of electrodes.

7. The system of claim 1, wherein the sensing elements comprise a polymer, optionally wherein the polymer is at least one of polylactic acid, poly(lactic-co-glycolic) acid, poly(caprolactone), polyglycolide, polylactide, polyhydroxobutyrate, polyhydroxyalcanoic acid, chitosan, hyaluronic acid, a hydrogel, poly(2-hydroxyethyl-methacrylate), poly(ethylene glycol), poly(L-lactide) (PLA), poly (dimethysiloxane) (PDMS), poly(methylmethacrylate) (PMMA), poly(glycerol sebacate), poly(octamethylene maleate (anhydride) citrate) (POMaC), POMaC without citric acid, poly(£-caprolactone), polyurethane, silk, a nanofabricated material, a co-polymer, a blended polymer, or a combination thereof or the polymer has mechanical properties tunable during a polymerization reaction.

8. The system of claim 7, wherein the polymer is POMaC.

9. The system of claim 1, wherein the sensing elements are porous, thereby permitting delivery of nutrients and growth factors to the tissue.

10. The system of claim 1, wherein the sensing elements have an elasticity from about 20 kPa to 0.5 MPa, or wherein the sensing elements has a wire shape.

11. The system of claim 1, wherein the well is configured to have a longitudinal axis, optionally wherein the sensing elements have an orientation that is perpendicular, parallel, or diagonal relative to the longitudinal axis of the well.

12. The system of claim 1, wherein the substrate comprises a polymer, optionally wherein the polymer is rigid or the polymer is polystyrene or polycarbonate.

13. The system of claim 1, wherein the cells are seeded in a hydrogel, or wherein the cells are selected from cardiomyocytes, fibroblasts, skeletal muscle cells, hepatocytes, renal cells, chondrocytes, skin cells, contractile cells, blood cells, immune system cells, germ cells, neural cells, epithelial cells, hormone secreting cells, bone marrow cells, stem cells, tumor cells, smooth muscle cells, endothelial cells, fibroblasts, adipose derived stem cells, mesenchymal stem cells, progenitor cells, or a combination thereof.

* * * * *